United States Patent

Mongeon et al.

[11] Patent Number: 5,954,752
[45] Date of Patent: Sep. 21, 1999

[54] CARDIOVERSION ENERGY REDUCTION SYSTEM

[75] Inventors: Luc R. Mongeon; Michael R. S. Hill, both of Minneapolis, Minn.

[73] Assignee: Medtronic, Inc., Minneapolis, Minn.

[21] Appl. No.: 08/846,938

[22] Filed: Apr. 30, 1997

[51] Int. Cl.$^6$ ........................................... A61N 1/39
[52] U.S. Cl. ................................................. 607/6
[58] Field of Search ..................... 607/5, 6, 7, 8, 607/23

[56] References Cited

U.S. PATENT DOCUMENTS

| | | |
|---|---|---|
| 5,074,301 | 12/1991 | Gill . |
| 5,314,448 | 5/1994 | Kroll et al. . |
| 5,366,485 | 11/1994 | Kroll et al. . |
| 5,500,004 | 3/1996 | Ansourian et al. . |
| 5,549,642 | 8/1996 | Min et al. . |

OTHER PUBLICATIONS

Allessi et al, "Regional Control of Atrial Fibrillation by Rapid Pacing in Conscious Dogs", published in *Circulation*, vol. 84, No. 4, Oct. 1991, pp. 1689–1697.

*Primary Examiner*—Scott M. Getzow
*Attorney, Agent, or Firm*—Reed A. Duthler; Harold R. Patton

[57] ABSTRACT

In an implantable pacemaker\cardioverter\defibrillator, a system for correlating the delivery of an atrial cardioversion therapy to an optimum blood pressure to effect delivery of the therapy when the volume of the atrium is minimized. In a first embodiment, the blood pressure in the atrium or ventricle is monitored and delivery is timed to a low blood pressure occurring as blood is emptying from the atrium. In a variation ventricular pacing may be provided to ensure that the ventricles are contracting forcefully and at a rate which optimizes atrial emptying. In a second embodiment, the delivery of the cardioversion therapy is also timed to an optimum point or phase of the respiratory cycle. The optimum point or phase of the respiration cycle depends in part on the chamber to be cardioverted and the location of the cardioversion electrodes with respect to the chamber.

57 Claims, 11 Drawing Sheets

CARDIOVERSION ENERGY REDUCTION SYSTEM

CROSS-REFERENCE TO RELATED APPLICATIONS

Reference is hereby made to commonly assigned, co-pending U.S. patent application Ser. No. 08/230,578 filed Apr. 21, 1994, for TREATMENT OF ATRIAL FIBRILLATION by Luc R. Mongeon et al.; Ser. No. 08/495,251 filed Jun. 27, 1995, for DEFIBRILLATION THRESHOLD REDUCTION PACING SYSTEM by Xiaoyi Min et al.; Ser. No. 08/230,577 filed Apr. 21, 1994, for METHOD AND APPARATUS FOR TREATMENT OF ATRIAL FIBRILLATION by William J. Combs et al.; Ser. No. 08/640,046 filed Apr. 30, 1996, for ATRIAL FIBRILLATION PREVENTION PACING SYSTEM by Rahul Mehra; and Ser. No. 08/846,747 filed on even date herewith for CARDIOVERSION ENERGY REDUCTION SYSTEM by Min et al.

FIELD OF THE INVENTION

The present invention generally relates to implantable cardioverter-defibrillators and particularly to a system for correlating the delivery of a cardioversion therapy to an optimum blood pressure of the heart chamber to be cardioverted and optionally at an optimum phase of the respiratory cycle of the patient to effect delivery of the therapy when the impedance between the cardioversion electrodes is minimized.

BACKGROUND OF THE INVENTION

By way of definition, in the field of automatic implantable arrhythmia control devices, the term "cardioversion" or "cardioverter" refers to the process of and device for discharging relatively high energy electrical shocks in excess of 1.0 Joule into or across cardiac tissue to arrest or "cardiovert" a tachyarrhythmia of a cardiac chamber. Delivery of cardioversion shocks may or may not be synchronized with a cardiac depolarization or rhythm and may be applied to arrest a malignant atrial or ventricular tachycardia or fibrillation with a selectable or programmable pulse energy. The termination of high rate tachycardias with lesser energy electrical pulses or bursts has also been referred to as "cardioversion" The arrest of atrial or ventricular fibrillation by higher energy shocks is referred to as "defibrillation", and defibrillation have been characterized in the past as a form of cardioversion. Products have been described and sold as "implantable cardioverter/defibrillator" (ICD) systems for providing synchronized cardioversion shocks or and unsynchronized defibrillation shocks and as "pacemaker/ cardioverter/defibrillator" (PCD) systems for providing additional staged therapies of anti-tachyarrhythmia pacing, synchronized cardioversion shocks and unsynchronized defibrillation shocks. In the following description and claims, it is to be assumed that the terms "cardioversion" and "defibrillation" and variants thereof are interchangeable, and that use of one term is inclusive of the other device or operation, unless specific distinctions are drawn between them in the context of the use. For convenience, the term "cardioversion" or "cardioversion/defibrillation" will be used unless a form of defibrillation therapy is specifically referred to.

Tachyarrhythmias are episodes of high rate cardiac depolarizations, typically occurring in one chamber of the heart but which may be propagated from one chamber to the other, and are distinguished from sinus tachycardias that physiologically accompany exercise to provide adequate cardiac output. Tachyarrhythmias that are sufficiently high in rate and chaotic compromise cardiac output from the affected chamber(s), leading to loss of consciousness and death, in the case of ventricular fibrillation, or weakness and dizziness, in the case of atrial fibrillation or flutter and non-sinus atrial and ventricular tachycardias. Atrial fibrillation and flutter are debilitating, due to the loss of atrial cardiac output contribution and interference with ventricular filling, but not immediately life threatening unless it leads to ventricular fibrillation. High rate atrial and ventricular tachycardias may exhibit a more organized rhythm but also may disable the patient and can lead to fibrillation if untreated.

Fibrillation has generally been treated by means of high energy cardioversion/defibrillation shocks, which, in the context of implantable anti-arrhythmia devices, are applied by means of large surface area cardioversion electrodes, including an electrode on or in the chamber to be defibrillated. The battery life of an ICD or PCD device depends on the amount of energy expended in delivering a therapy and the delivery frequency. The high energy level employed in order to defibrillate consumes considerable energy in the range of 1.0–30.0 Joules per delivered shock. The high energy level is employed in order to simultaneously depolarize the bulk of the heart chamber to be defibrillated, which will include tissues in all stages of the depolarization-repolarization cycle at the time the pulse is delivered.

For patients experiencing ventricular fibrillation, the delivered cardioversion/defibrillation shock energy is necessary to save the patient's life and is usually not perceived by the patient because of the loss of consciousness shortly following onset of the arrhythmia. Accuracy of diagnosis and delivery of a cardioversion shock having sufficient energy to cardiovert the rhythm as quickly as possible are paramount concerns because the efficacy of the shock decreases with time lapse from onset of the symptoms.

Patients experiencing high rate atrial tachycardias and atrial fibrillation/flutter typically do not lose consciousness, and the condition is usually not life threatening. The intentional or inadvertent delivery of the cardioversion shock therapy by an ICD or PCD device is startling and painful to a degree that is assumed to be proportional to the shock energy level.

It was recognized early in the development of external ventricular defibrillators that a lower energy synchronous cardioversion shock could be employed to interrupt a high rate ventricular tachycardia, if the shock delivery was synchronized to a ventricular depolarization event, i.e. the R-wave. The lower energy threshold is attributed to the assumption that more of the ventricular muscle mass is intrinsically depolarized at this time, thereby requiring less cardioversion energy to depolarize the remaining ventricular muscle mass. If synchronization to a ventricular depolarization or R-wave peak can be achieved, staged therapy ICD and PCD devices deliver somewhat lower energy cardioversion shocks to the affected chamber. In such ventricular synchronous cardioversion, a delay interval of about 100 ms from the preceding R-wave peak is employed to ensure that the "vulnerable period" associated with the re-polarization of the heart is past.

Episodes of atrial tachyarrhythmias occur frequently and are debilitating to the patient, if not life threatening. Unfortunately, the quantity of electrical energy required to cardiovert or defibrillate the atria is sufficient, in most cases, to cause a sudden, propagated pain in the patient's chest area or to stun the patient. Typically reported defibrillation thresholds (in humans) of 2–3 Joules are required between transvenous lead bearing electrodes placed to provide atrial cardioversion pathways between the right atrium (RA) and the coronary sinus (CS) or the superior vena cava (SVC) and the CS. Other atrial electrode systems may require up to 4.–10 Joules (in humans) to reliably cardiovert. Significant discomfort and often intolerable pain is associated with such atrial cardioversion/defibrillation shock therapies in this range, resulting in sedation of some patients and refusal to accept the therapy by other patients. Moreover, there is concern that the attempt to defibrillate the atria will itself induce ventricular fibrillation leading to the death of the patient. In the hospital setting, the patient is carefully monitored, and induced ventricular fibrillation may be defibrillated. However, the clinical procedure still entails enough risk that drug therapies are preferred, and atrial defibrillation is used only after other therapies fail.

The same concerns have delayed the development of implantable atrial defibrillators so that patients prone to bouts of atrial fibrillation or flutter could remain ambulatory. One possible approach that has been widely published is to combine the atrial and ventricular fibrillation detection and cardioversion/defibrillation capabilities in a single implantable system so that induced ventricular fibrillation could be terminated. Such a device is disclosed in U.S. Pat. No. 5,549,642, issued to Min et al. The Incontrol Metrix TM atrial defibrillator, currently in clinical evaluation, does not provide the capability of treating induced ventricular tachyarrhythmias and therefore relies upon shock delivery criteria to avoid induction of ventricular tachyarrhythmias.

In the context of atrial cardioversion, a proposed pacemaker/defibrillator is disclosed in PCT Publication No. WO 92/18198 by Adams et al. where the synchronization of the high voltage atrial cardioversion shock is to the R-wave in an effort to avoid inducing ventricular tachycardia or fibrillation. In any case, synchronization to an R-wave in a high rate, irregular EGM has proven to be difficult to accomplish and not always effective to avoid inducing ventricular fibrillation.

Faced with these difficulties, attempts have been made to first make the cardiac rhythm more regular so that the P-wave or R-wave may be detected and to then apply the synchronous cardioversion therapy. In commonly assigned U.S. Pat. No. 5,193,536, a PCD system is described where the high atrial or ventricular rate is made more regular by delivering overdrive pacing pulses to capture the heart and by using the last overdrive pulse delivered as a synchronization event to time the delivery of the cardioversion shock. Another method is disclosed in U.S. Pat. No. 5,074,301 where a single pacing pulse is delivered to the atrium to allow the cardioversion shock to be delivered in the atrial refractory period. It is not suggested that the overdrive pacing pulses affect the cardioversion threshold.

In U.S. Pat. Nos. 5,314,448 and 5,366,485, an ICD is described having a set of cardioversion electrodes arranged around the patient's heart. When fibrillation is detected, the high output capacitors begin to be charged. As they are charged or after full charge is achieved, a "pre-treatment" of the fibrillating heart muscle is commenced through the generation of a train of pulses from the voltage on the output capacitors and delivery of the pulses across the cardioversion electrodes. The capacitors are recharged and at the end of the recharge time period, the high energy cardioversion pulse is delivered across the cardioversion electrodes. It is stated that the pre-treatment pulses begin the process of organizing the chaotically contracting myocardial cells and result in a reduction of cardioversion threshold and the total energy expended. It is emphasized that the pre-treatment pulse voltages are well in excess of pacing level voltages and that the same cardioversion electrodes are employed to deliver the energy to the same myocardial cells as will be defibrillated by the cardioversion pulse. In this manner, the pre-treatment pulses are delivered into the high current density regions of the current pathways in the heart chamber between the spaced apart cardioversion electrodes.

In the above-referenced '251 application, a method and apparatus for terminating fibrillation is disclosed using a burst of pacing energy, high frequency pulses applied into a low current density region of the cardiac tissue in the chamber in fibrillation prior to the delivery of one or more cardioversion energy pulses. The burst of pacing energy pulses is delivered between the pace/sense electrodes located in the low current density region of the cardioversion pathway around and through the heart chamber defined by the cardioversion energy distributed between the spaced apart cardioversion electrodes. The burst of pacing energy pulses injected into the low current density region results in the lowering of the cardioversion threshold, and the decreased energy cardioversion pulse effectively terminates the fibrillation episode. The burst of pacing energy pulses appears to develop a refractory island in the low energy region of the heart chamber that may itself lower the cardioversion energy, and also appears to prevent ectopic beats originating in the low energy region from re-fibrillating the heart.

Recently, the theoretical possibility of employing low energy pacing level pulses (i.e. less than 0.05 joules) to terminate atrial fibrillation has been explored. For example, in the recent article "Regional Control of Atrial Fibrillation by Rapid Pacing in Conscious Dogs", by Allessie et al, published in *Circulation*, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site, is reported. However, the depolarization wavefront created by such pulses does not propagate through the entire chamber due to the varying polarization states of the tissue surrounding the stimulation site. Consequently, it has not been demonstrated that this approach can defibrillate a heart chamber actually in fibrillation.

It is generally believed that the delivery of pacing pulse bursts to the atrium can induce atrial fibrillation, unless the delivery is synchronized to P-waves to assure that the pulse bursts occur within the refractory period of the atrium. This effect is discussed in U.S. Pat. No. 5,334,221 which discloses a device which provides pulse bursts, synchronized to a P-wave, to the SA nodal fat pad in the atrium to reduce the sinus rate of patients who suffer from angina.

Despite this general belief, it has also been proposed to avoid synchronizing the delivered pacing pulse or burst to a detected depolarization to interrupt atrial fibrillation or flutter. In the '577 application, the pacing pulses are simultaneously delivered at multiple sites distributed over a substantial portion of the atria or atrium to be treated. Rather than attempt to synchronize the delivered pulses to the high rate atrial electrogram sensed at a stimulation site, simultaneous pulse delivery at the multiple dispersed sites is intended to eventually result in capture of the atrial tissue at one or more of the stimulation sites. It is theorized that the propagation of the depolarization wavefront created in response to the delivered pacing pulse, toward cardiac tissue closely adjacent the site at which capture initially occurs, increases the probability that the adjacent tissue will be in an appropriate stage of the depolarization-repolarization cycle to be captured by the next pulse in the burst. As pulses of the burst continue to be delivered, therefore, the amount of atrial tissue captured should gradually increase, with the end result of capturing a sufficient amount of atrial tissue to terminate fibrillation.

Similarly, in the '578 application, a series of low energy pulse bursts is delivered, separated by defined inter-burst intervals, and including bursts unsynchronized to atrial heart depolarizations. Detection of termination of atrial fibrillation during inter-burst intervals results in cancellation of further pulse bursts to prevent re-induction of fibrillation.

Despite these advances, a need continues to exist for atrial and ventricular cardioversion systems that can cardiovert high rate atrial and ventricular tachycardias and atrial fibrillation/flutter at lower energy levels to decrease energy consumption and pain perceived by the patient.

SUMMARY OF THE INVENTION

It is therefore an object of the present invention to provide cardioversion/defibrillation method and apparatus that operates to cardiovert with lower energy cardioversion pulses. The present invention is directed to the termination of an atrial tachyarrhythmia when the atrial volume is minimized by deflation of the chamber during rapid ventricular filling and, optionally at an optimum point or phase of the respiratory cycle.

The invention is directed, in a first embodiment, toward providing a method and apparatus for cardioverting tachyarrhythmia of a heart chamber using termination therapies of the types described above delivered when the chamber is subjected to deflation in volume due to emptying of blood from the chamber to thereby reduce therapy energy necessary to achieve cardioversion of the chamber and to consequently reduce the pain perceived by the patient and premature depletion of the power source.

In a particular application of the first embodiment, cardioversion of high rate atrial tachycardias such as atrial fibrillation or flutter is addressed. Deflation of the atria occurs during passive filling of the ventricles from the atria. The pulsatile pressure of the atria is at minimum at this point, as is the right ventricular pressure. The deflation of the atria is accompanied by an increase in volume impedance between the atria and the surrounding pleural sac and lungs that helps to ensure that the shock current pathways are concentrated in the atrial wall. In one embodiment, the delivery of the therapy may be timed to a detected minimal right atrial or right ventricular blood pressure level (measured directly or indirectly), signifying that the right ventricle is fully relaxed. In the case of atrial fibrillation, the atria are not physically contracting, so that emptying of the atria occurs as a result of relaxation of the ventricles. In this context, the efficiency of the ventricles in emptying the atria affects the volume of blood in the atria, with increased efficiency in emptying the atria manifested by a decrease in minimum atrial pressures. The atrial pressure minimums still occur during the passive filling phase following the paced or sensed ventricular contractions.

In a variation of the first embodiment, ventricular pacing during atrial fibrillation may be provided to ensure that the ventricles are contracting at a rate which optimizes emptying of the atria to reduce atrial volumes and pressures. The ventricular pacing rate is gradually incremented as the right atrial pressure is monitored to determine a pacing rate which results in desirably low atrial pressure measurements, which may be defined, for example, as the lowest ventricular pacing rate which results in a minimal atrial blood pressure less than a defined minimum value. Cardioversion/defibrillation therapy is thereafter delivered, preferably synchronized to a an occurrence of a minimum atrial blood pressure value which occurs outside the vulnerable period of the ventricles.

A second embodiment of the invention takes advantage of the fact that the chamber volume and the autonomic tone for sustenance of fibrillation of the atria are also influenced by the respiratory cycle, by timing the delivery of the cardioversion therapy to occur at a selected point or phase of the respiratory cycle. The pleural pressure variations associated with respiration are mirrored by the atrial pressure, with minimum pulsatile pressure and average atrial pressure increasing with increasing pleural pressure. In addition, cardiac sympathetic and parasympathetic nerve activity, which also affects defibrillation thresholds also vary with respiration. The cardioversion or defibrillation pulse is preferably not delivered during expiration, when cardiac parasympathetic (vagal) nerve activity is at a maximum. The point or phase of the cycle for delivery of the cardioversion/defibrillation shock may be chosen to occur at the endpoint of expiration or more preferably during inspiration so that the diaphragm is contracting or contracted not susceptible to being stimulated to produce an unexpected inspiration. The selected delivery time may also be chosen to occur during the phase of inspiration when cardiac sympathetic nerve activity is increased.

In a first application of this second embodiment, particularly valuable for use with cardioversion electrodes located substantially in contact with the heart chamber, the cardioversion/defibrillation pulse is delivered at the end of inspiration. In a second application of this second embodiment, particularly valuable for use with one or more cardioversion electrodes located substantially in contact with the heart chamber and a remote electrode, the cardioversion/defibrillation pulse may be delivered at the onset of inspiration.

Advantageously, in these applications combining the considerations of the respiratory cycle and the intracardiac blood pressure, the perception of pain attendant a cardioversion shock delivery may be lessened. In addition to reductions in pain due to reductions in cardioversion/defibrillation pulse level, delivery of the cardioversion/defibrillation pulse during the interval in which the diaphragm is contracted avoids discomfort associated with diaphragmatic stimulation.

Furthermore, the cardioversion therapy may optionally comprise any of the efficacious combinations of cardioversion/defibrillation shocks, pre-treatments or anti-tachycardia pacing therapies described above and elsewhere in the continuing development of the field of atrial and ventricular cardioversion. In the event that synchronization to the minimum blood pressure and/or the end inspiration point or phase is not possible over a given number of attempts or maximum therapy time period, an unsynchronized therapy may be delivered.

While the invention is believed primarily beneficial in the cardioversion of atrial fibrillation, as a practical matter, it may be difficult to distinguish atrial fibrillation from atrial flutter or high rate atrial tachycardias which may be simultaneously present in some patients. It is believed that the methods and apparatus of the present invention are beneficial in terminating any such atrial tachyarrhythmia.

The present invention also has general application to the delivery of ventricular cardioversion therapies to the ventricles to treat ventricular tachyarrhythmias, particularly high rate ventricular tachycardias where the patient is conscious and/or breathing, as described above. However, the delivery of the prescribed therapy cannot be unduly delayed in the attempt to synchronize the delivery to the appropriate point or phase of the respiratory cycle.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
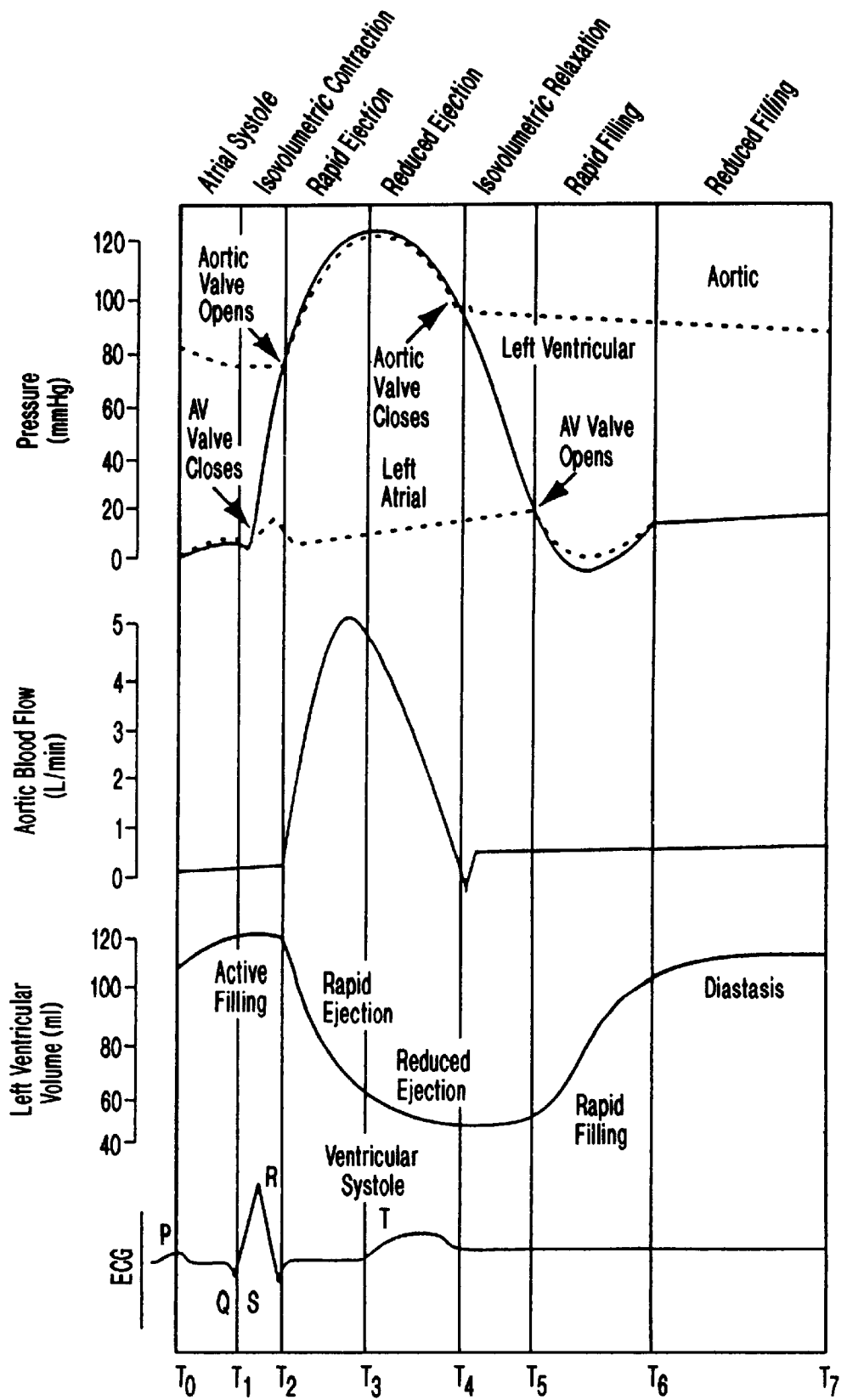
FIG. 1 is a graphical depiction of the cardiac cycle attendant depolarization of the heart chambers and attendant atrial and ventricular pressure waves.
Figure 2:
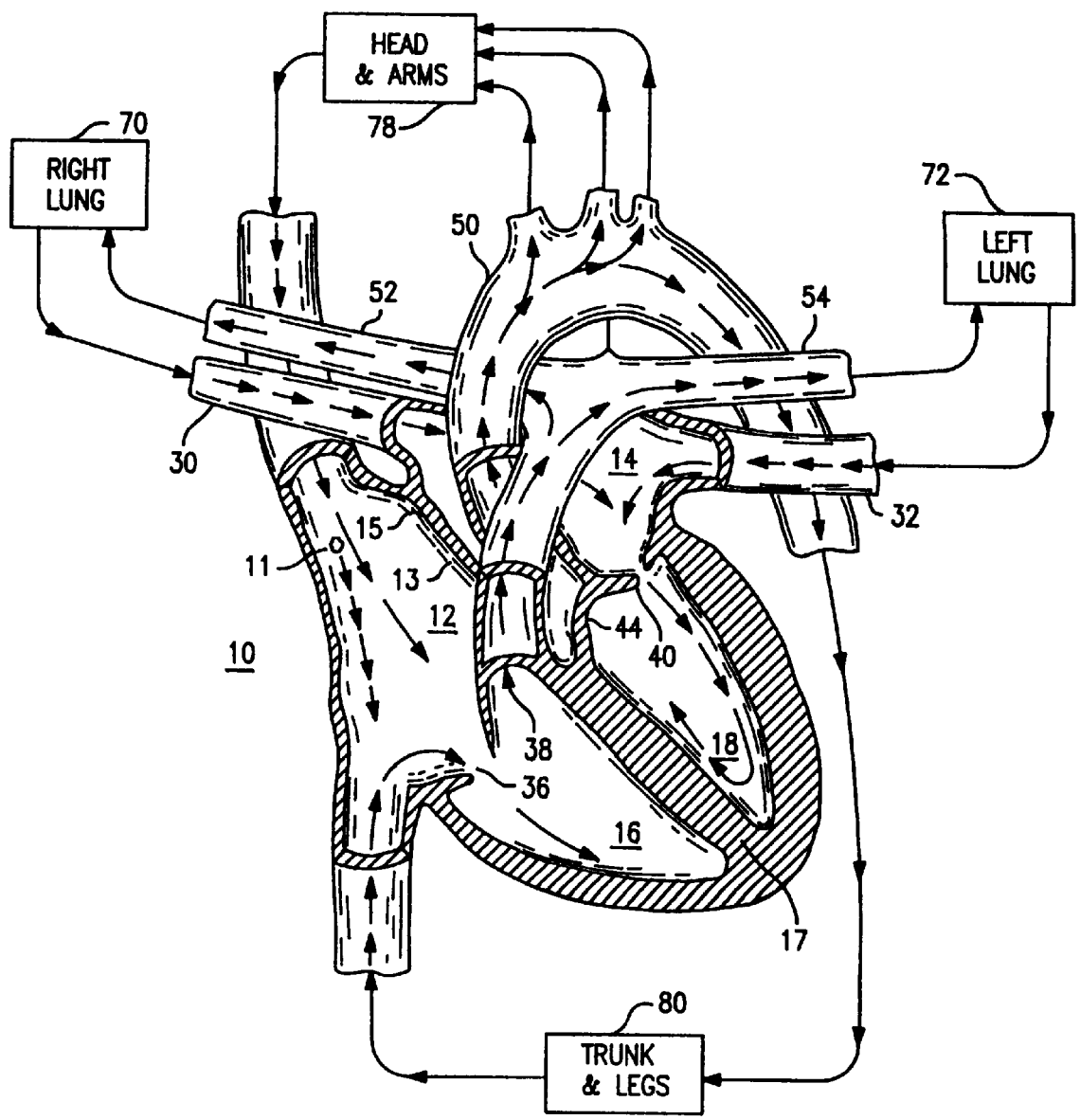
FIG. 2 is a view of the chambers of the heart and the cardiac vessels in the circulatory system during contraction of the atria in an atrial depolarization to fill the ventricles with blood pooled in the atria from the circulatory system.
Figure 3:
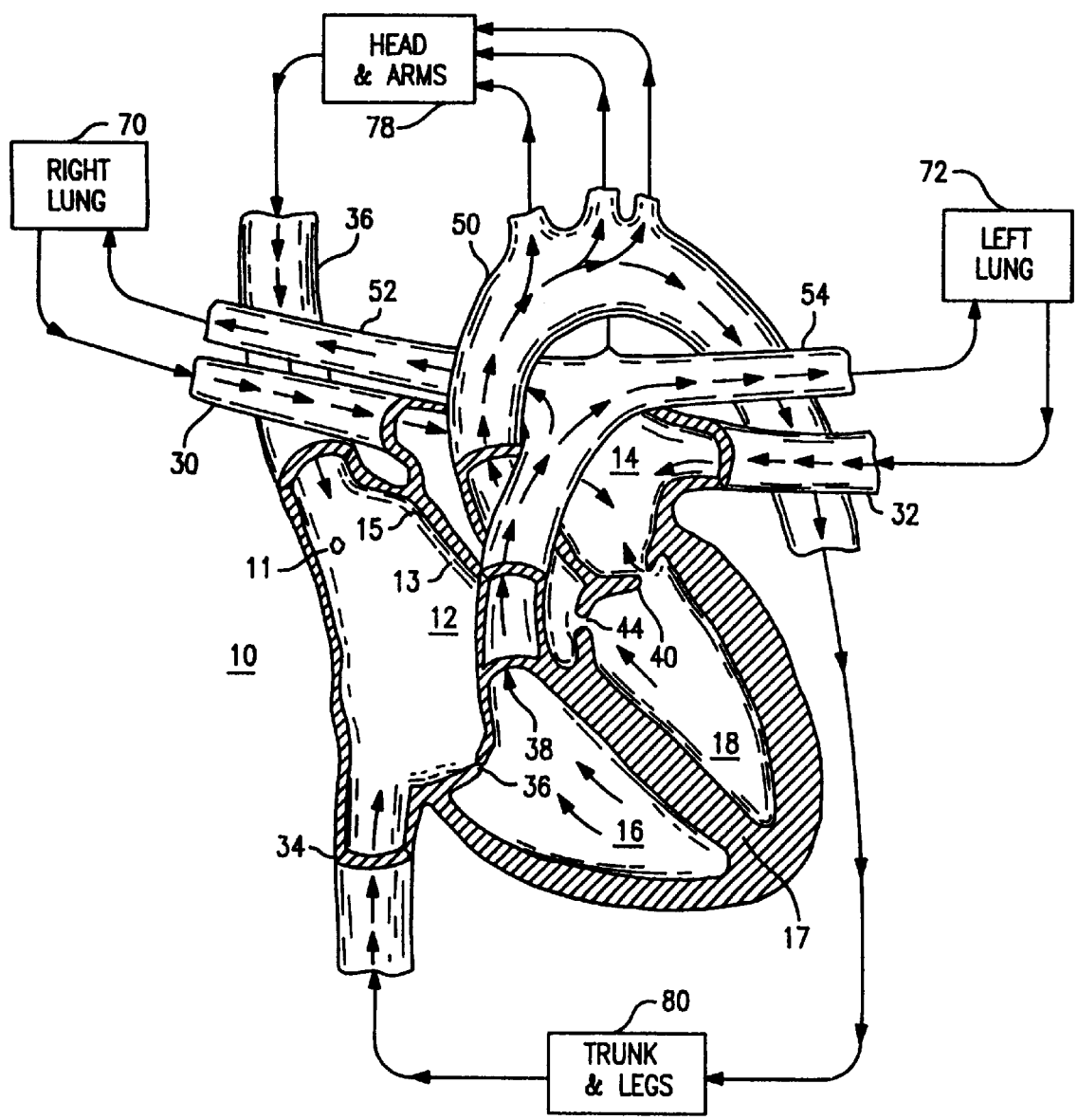
FIG. 3 is a view of the chambers of the heart and the cardiac vessels in the circulatory system during contraction of the ventricles to expel blood into the circulatory system.

Before describing the preferred embodiments and variations of the invention, attention is directed to FIGS. 1–3 that depict the cardiac circulatory system and synchronized depolarizations of the heart chambers. In FIG. 1, the electrical depolarization waves attendant a normal sinus rhythm, intrinsic heart cycle or beat are depicted in relation to the fluctuations in absolute pressure, aortic blood flow and ventricular volume in the left heart. The right atrium and ventricle exhibit similar pressure, flow and volume fluctuations. FIGS. 2 and 3 depict the contractions of the atria and the ventricles represented by the P-wave and the QRST complex in FIG. 1 during normal sinus rhythm. In accordance with one aspect of the present invention, it is recognized that in high rate atrial tachycardia or atrial fibrillation/flutter accompanied by independent ventricular function, the atria do not actively contract but are still reduced in volume and atrial blood pressure is reduced when atrial blood empties into the ventricles in the passive filling phase. This reduction in of atrial blood pressure can be measured and employed in timing the delivery of the atrial cardioversion therapy according to the present invention. Ventricular blood pressure is also at a minimum during the passive filling phase, and may also be employed in timing the delivery of the atrial cardioversion therapy according to the present invention. In one application of the invention, the ventricular pacing rate may be selected to improve the ventricles' efficiency in emptying the atria with resultant decreases in atrial volumes.

FIG. 2 is a view of the chambers of the heart 10 and the cardiac vessels in the circulatory system during a normal contraction of the right and left atria 12 and 14 in an atrial depolarization propagated from an S-A node 11 and detected as the P-wave in FIG. 1. In FIG. 2, the atrial depolarization propagates through the atrial walls of the right and left atria 12 and 14 and toward an A-V node 13 above the junction of the atrial septum 15 separating the atrial chambers and the ventricular septum 17 separating the ventricular chambers. The S-A node 11 is located high in the right atrial wall and is influenced by nerve fibers from the autonomic nervous system to depolarize at a rate correlated to the need for cardiac output.

Venous return blood from the lower and upper body enters the right atrium 12 through the inferior vena cava 34 and the superior vena cava 36. Oxygenated blood returns from the right and left pulmonary veins 30 and 32 from the right and left lungs 70 and 72, respectively. Upon relaxation of the right ventricle 16, the tricuspid valve 36 opens, and venous blood pooled in the right atrium enters the right ventricle 16. Similarly, oxygenated blood in the left atrium 14 enters the left ventricle 18 through the mitral valve 40 which is opened by relaxation of the left ventricle 18. The pulmonary valve 38 and the aortic valve 44 remain closed as the relaxed ventricles 16 and 18 fill with blood. This is known as the passive ventricular filling phase.

The contraction of the atria 12 and 14 in normal sinus rhythm continues to further fill the right and left ventricles 16 and 18 with blood previously pooled in the atrial chambers 12 and 14 from the circulatory system. This is known as the active ventricular filling phase, and does not occur during atrial fibrillation or flutter during which the atrium is not actively contracting.

In FIG. 3, in normal sinus rhythm the ventricles 16 and 18 contract a short A-V conduction time after the atria. In the case of atrial fibrillation or flutter in which the atria are not actively contracting, the ventricles may contract at a rate determined by intermittent conduction of atrial depolarizations. The contractions of the right and left ventricles 16 and 18 force closed the tricuspid valve 36 and the mitral valve 40 while forcing open the pulmonary valve 38 and aortic valve 44. In FIG. 1, the QRS depolarization wave or R-wave represents the near synchronous depolarization wave and the beginning of mechanical contraction of the ventricular myocardial cells. The following T-wave accompanies the repolarization and beginning of relaxation of the ventricular myocardial cells of the ventricles 16 and 18. The right and left ventricular blood pressure waves lag the R-wave. Venous blood is propelled by the forceful contraction of the right ventricle 16 through the right and left pulmonary artery branches 52 and 54 of the pulmonary artery and into the lungs 70 and 72. Oxygenated blood is propelled through the open aortic valve 44 and the aorta to vessels in the head and arms 78 and trunk and legs 80.

The cardiac cycle is completed in the interval between successive PQRST complexes and following relaxation of the atria and ventricles as the right and left atria 12 and 14 re-fill with venous blood and oxygenated blood while the tricuspid valve 38 and the mitral valve 40 remain closed. In sinus rhythm, the interval between depolarizations may be on the order of 500.0 ms to 1,000.0 ms for a corresponding sinus heart rate of 120 bpm to 60 bpm, respectively.

When the atria 12 and 14 are in fibrillation or flutter, atrial cells depolarize randomly and independently of the S-A node 11. The atria 12 and 14 no longer contract coherently to achieve active ventricular filling by expelling pooled blood into the respective ventricles 14 and 16. As pooled atrial blood volume increases, atrial blood pressure within the atrial chambers may rise and the atrial walls may be distended. The post-contraction relaxation of ventricles 16 and 18 combined with the build-up of atrial blood volume and pressure causes the tricuspid valve 36 and the mitral valve 40 to open to allow at least partial filling of the ventricles. The ventricles 16 and 18 continue to contract periodically due to spontaneous depolarizations from the A-V node 13, and blood circulation is maintained, but without atrial contribution.

In the absence of synchronous atrial and ventricular contractions, the ventricular depolarization rate or overall heart rate is somewhat uncoupled from the autonomic system that regulates heart rate as a function of the body's need for cardiac output. The ventricles 16, 18 depolarize or beat at spontaneous rates determined by the AV node or at rates determined by intermittent conduction of atrial depolarizations to the ventricle. One way to increase cardiac output and provide a stable heart rate is to overdrive the ventricles 16 and 18 through pacing at a rate that exceeds the intrinsic ventricular depolarization rate. This higher pacing rate improves the efficiency of the ventricles in emptying the atria and thereby decreases the buildup of atrial pressure and the distention of the atrial walls.

When an atrial cardioversion therapy is delivered to the atria 12 and 14, it must be of sufficient energy that the current distributed in current pathways between the cardioversion electrodes is great enough to substantially simultaneously depolarize most of the atrial myocardial cells so that synchronous atrial repolarization may occur and a new depolarization may be initiated by the S-A node 11. When the atrial walls are distended, effective refractive periods (ERPs) decrease, the dispersion of refractoriness increases, the cardioversion shock current pathways lengthen, impedance increases, and the cardioversion threshold is elevated. Conversely, we have determined that the cardioversion threshold may be reduced by timing the delivery of the atrial cardioversion therapy to a time when the atria are not distended or are subjected to a reduction in volume to thereby reduce cardioversion therapy energy necessary to achieve cardioversion (defibrillation) of the atria and to consequently reduce the pain perceived by the patient. The therapy may be delivered across atrial cardioversion electrodes placed in various locations in relation to the atria.

During high rate atrial tachycardia or atrial fibrillation/flutter, the state of expansion and contraction or compression of the atria can be determined from right atrial or right ventricular absolute blood pressures which in this case vary as a function of the opening and closing of the tricuspid valve 36, the ventricular contraction and relaxation, and the external influence of the respiratory cycle. In one embodiment of the invention, it is recognized that the reduction in volume of the atria 12, 14 occurs in high rate atrial tachycardias and atrial fibrillation/flutter upon emptying of atrial blood into the associated ventricles 16, 18 following the ventricular contraction. The deflation of the atria 12, 14 accompanying the opening of the tricuspid valve (at the time of opening of the AV valve in FIG. 1) provides a pronounced reduction in atrial blood pressure and deflation of the atria, even when an atrial tachyarrhythmia is present.

Therefore, in an example of the first embodiment, the right atrial blood pressure is measured by an absolute blood pressure sensor introduced into the right atrium 12 or right ventricle 16. The delivery of the cardioversion therapy is timed to a minimal measured blood pressure level, shown between times $T_5$ and $T_6$ in FIG. 1, signifying that the right ventricle 16 has previously contracted (during times $T_2$ and $T_5$ of FIG. 1) to expel blood into the pulmonary artery branches 52, 54 and is in a relaxation phase. At this time, the tricuspid valve 36 (AV Valve in FIG. 1) is open, allowing the pooled right atrial blood to passively flow into the right ventricle 16. At the same time, pooled blood in the left atrium 14 is flowing through the opened mitral valve 40 to passively fill the left ventricle 18. This delivery may also be correlated in time to the preceding ventricular sense from a pace/sense electrode within the right ventricle 16, and clearly follows the T-wave between times $T_3$ and $T_4$ of FIG. 1.

In a variation of this embodiment, ventricular pacing may be provided through the ventricular pace/sense electrode to ensure that the ventricles 16, 18 are contracting at a rate selected to produce efficient emptying of the atria. In a diagnostic sequence, the ventricular pacing rate is varied as the right atrial pressure is monitored to determine an optimum relation between pacing rate and the minimal measured right atrial pressure. The atrial cardioversion shock is delivered in timed relation to a detected minimal atrial blood pressure at a time outside the ventricular vulnerable period.

In the second embodiment of the invention, it is recognized that the contraction or compression of the atria 12, 14 due to respiratory inspiration may be accompanied by reduced autonomic tone for the sustenance of atrial fibrillation/flutter, and an impedance plethysmography method is employed to detect the respiratory cycle of the patient. When cardioversion electrodes on or in the heart are employed, the cardioversion/defibrillation pulse is preferably delivered at the end of inspiration, when increase in lung volume is associated with a decrease in atrial volume, cardiac parasympathetic (vagal) nerve activity is at a minimum and the diaphragm is fully contracted so that it cannot be stimulated by the delivered pulse. When at least one remote cardioversion electrode is employed, the cardioversion/defibrillation pulse is delivered in response to the end of expiration, for example at the onset of inspiration, assuming that the impedance between the cardioversion electrodes is lowered by the contraction of the space between them. Typically, the remote cardioversion electrode is implanted subcutaneously and may constitute the case of the PCD.

Figure 4:
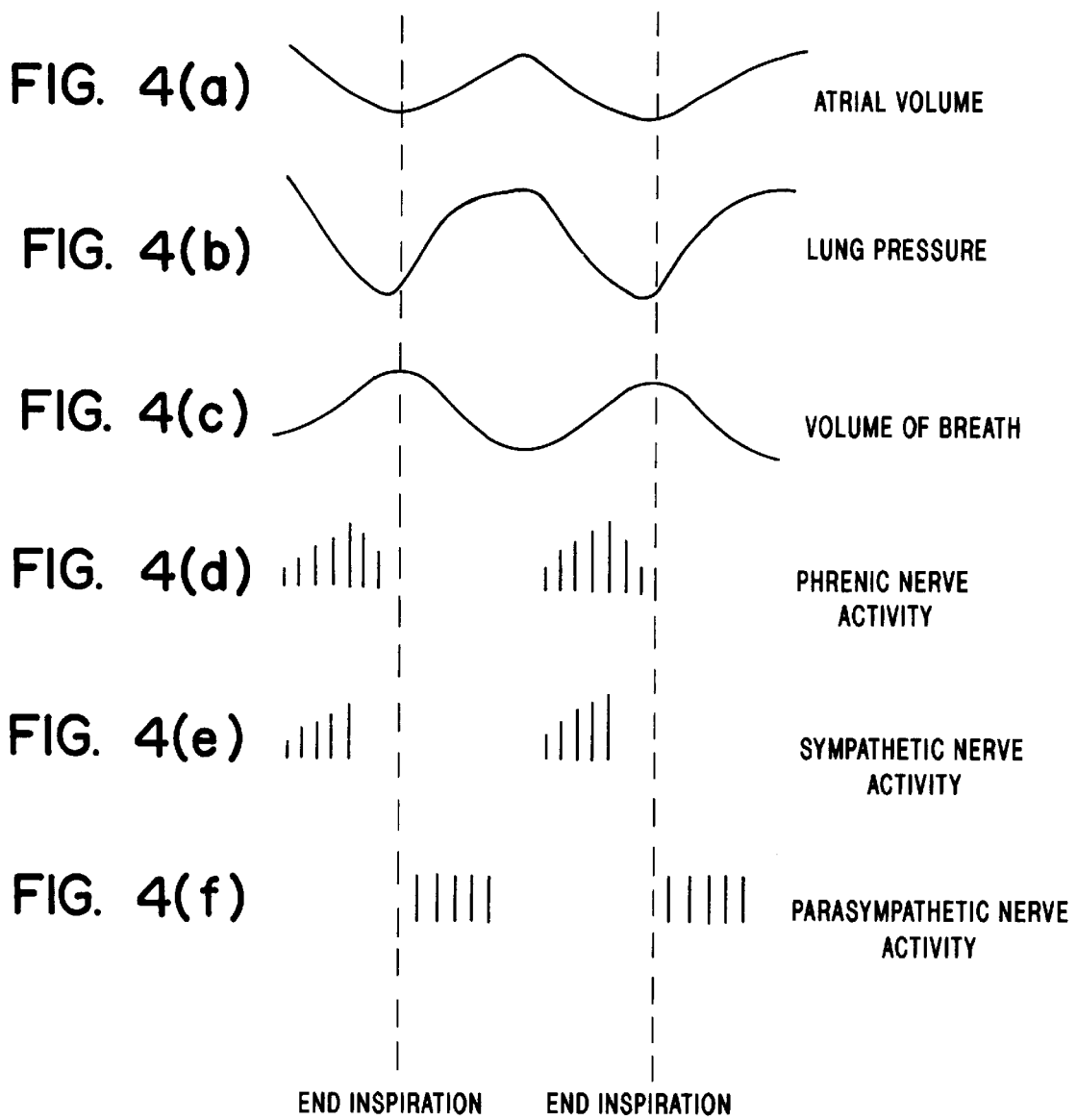
FIG. 4 is a graphical depiction of the respiratory cycle and the pressure waves, volume waves and nerve activity attendant to breathing.

This second embodiment may be implemented in combination with the variations of the first embodiment as discussed below. In Such cases, cardioversion/defibrillation pulses may be delivered to the atria at a detected minimal atrial pressure during the desired point or phase of the respiratory cycle, outside the vulnerable period of the ventricles. It should also be noted that while the beginning and endpoints of inspiration and expiration may be determined from an impedance plethsymograph signal, it should be possible to monitor the respiratory cycle into account from the fluctuations of the right atrial pressure over a number of cardiac cycles, as the atrial blood pressure fluctuates with the intra-pleural pressure as illustrated in FIG. 4. As described below, the first and second embodiments may also be adapted to systems for timing the delivery of ventricular cardioversion therapies to the minimum ventricular volume particularly for cardioversion of ventricular tachyarrhythmias that still exhibit a somewhat organized ventricular contraction that empties blood during a cardiac cycle, e.g. high rate ventricular tachycardia.

Turning to FIG. 4, it represents the lung pressure and air volume waveforms of respiratory cycles and their affect on atrial volume as well as attendant nerve signal bursts to the heart that the intrinsic heart rate and excitability of myocardial cells to the respiratory cycle. In each respiratory cycle, and as shown in tracing (c), the air volume in the lungs increases from a start inspiration point to a maximum at an end inspiration point and then decreases during expiration to an end expiration point, where it may remain until the next start inspiration point. The inspiration phase of the respiration cycle is effected by contraction of the diaphragm in response to the phrenic nerve firings shown in tracing (d) which continue until the end inspiration point. The inspiration phase is also accompanied by the sympathetic nerve firings that are shown in tracing (e). The expiration phase is accompanied by parasympathetic nerve firings shown in tracing (f). The atria respond to the sympathetic nerve firings by increasing excitability, thereby making them easier to cardiovert or defibrillate. Somewhat conversely, the atria respond to parasympathetic nerve firings by shortening refractory intervals, which can have the effect of decreasing a prevailing AF cycle length, making the atria more difficult to cardiovert or defibrillate. As such in the second embodiment of the present invention, the cardioversion/defibrillation shock is timed to occur outside the expiration phase.

As shown in tracing (c) of FIG. 4, during inspiration the volume of air in the lungs increases due to decreased lung pressure as shown in tracing (b), drawing air into the lungs. The volume of the atria shown in tracing (a) can also vary with the lung volume so that the atrial volume is also decreased at the end inspiration point. In the second embodiment of the present invention, delivery of an atrial cardioversion/defibrillation therapy, particularly between atrial cardioversion electrodes substantially in contact with the heart, is timed to the detection of the end inspiration point or the inspiration phase leading up to the end inspiration point. The respiration cycle normally takes several seconds to complete, and the inspiration point can be prolonged by holding one's breath, for a matter of seconds. The ventricular cardiac cycle shown in FIG. 1 varies between 0.5 seconds (120 bpm) at moderate exercise or excitement and 1.0 seconds (60 bpm) at rest, and consequently several cardiac cycles may be completed during the respiratory cycle and during an end inspiration point maintained by holding one's breath. Thus the delivery of a cardioversion/defibrillation therapy at a measured low atrial blood pressure point during the end of inspiration is employed in accordance with this aspect of the present invention.

Figure 5:
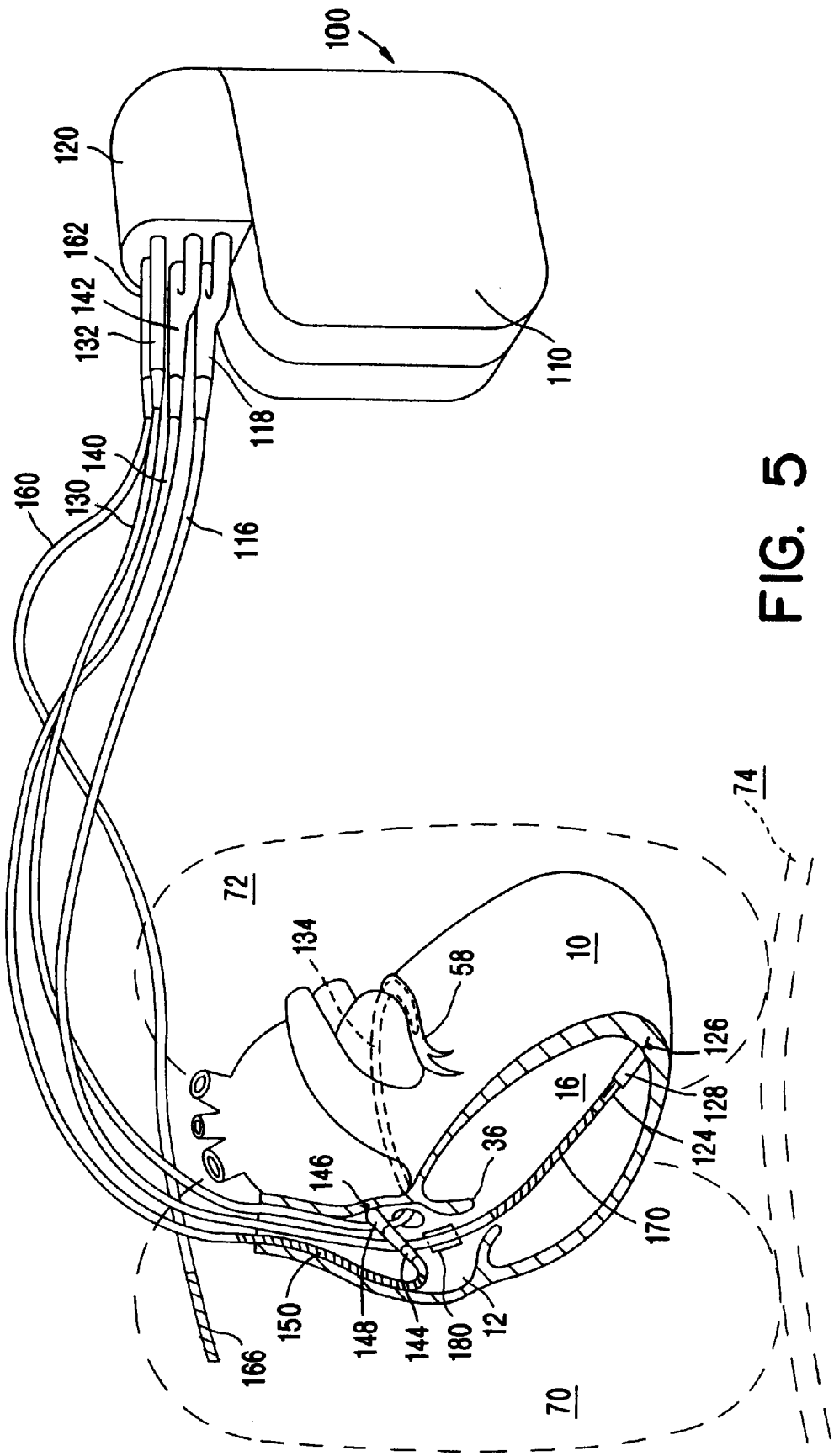
FIG. 5 is a schematic view of an illustrative comprehensive ICD or PCD implantable pulse generator (IPG) and lead system in which the embodiments and variations of present invention may be advantageously selectively employed or combined.
Figure 6:
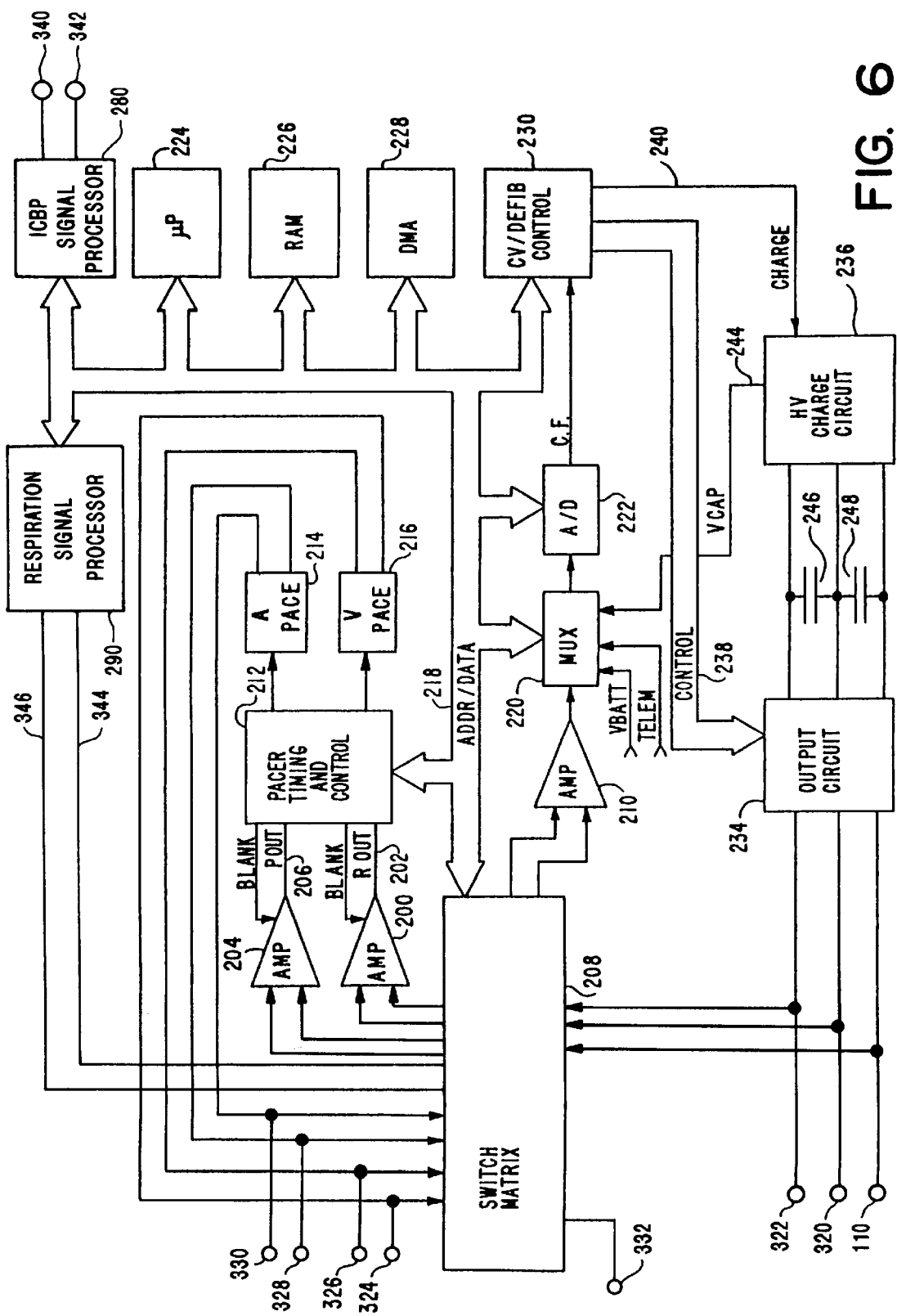
FIG. 6 is a system block diagram of a comprehensive ICD or PCD IPG of the type in which the embodiments and variations of present invention may be advantageously selectively employed or combined.

The embodiments of the invention are preferably implemented in the context of a PCD system having single or dual chamber pacing and/or cardioversion/defibrillation capabilities of the types described in detail in the above-referenced '441 patent and in commonly assigned, U.S. Pat. No. 5,549,642, respectively, incorporated herein by reference in their entireties. Such PCD IPGs may be constructed or made programmable to provide atrial only, ventricular only, or both atrial and ventricular pacing modes. The pacing modes also preferably include either or both bradycardia compensating pacing modes or anti-tachycardia pacing therapies. In addition, the present invention may be employed with a wide variety of cardioversion electrode combinations for atrial or ventricular cardioversion FIGS. 5 and 6 illustrate a dual chamber, multi-programmable, PCD IPG 100 and associated lead system for providing atrial and ventricular sensing functions for detecting P-waves of atrial depolarizations and R-waves of ventricular depolarizations, depending on the programmed pacing and/or sensing mode and providing atrial or ventricular cardioversion therapies. An exemplary cardioversion lead system and electrodes are depicted in FIG. 5 for delivering atrial cardioversion/defibrillation shock or other therapies to the atria 12, 14 or the ventricles 16, 18 of the heart 10. The heart 10 is illustrated in relation to the right and left lungs 70 and 72 and the diaphragm 74. The lead system also includes impedance sensing lead 160 having at least one electrode 166 at the distal end of the lead 160 positioned across the patient's chest from the location of the IPG 100. The electrode 166 and the IPG can electrode 110 may be used to derive a respiration signal from impedance changes in the current pathway between them that varies with the expansion and contraction of the lungs 70, 72 and chest attendant to inspiration and expiration of air into and from lungs 70 and 72. The IPG can electrode 110 and any one of the illustrated cardioversion electrodes may alternatively be used to derive the respiration signal. FIGS. 5 and 6 are intended to provide a comprehensive illustration of each of the components sufficient to operate in accordance with each of the embodiments and variations of the invention in relation to the patient's cardiovascular and respiratory system in configurations that may be effected using subcombinations of the components depicted therein and equivalents thereto.

In the preferred embodiment of FIGS. 5 and 6, depending on the programmed pacing mode, pacing pulses may be applied to the atrium and/or ventricle in response to the detection of the appropriate bradycardia condition by the PCD IPG 100. The pacing and sensing functions are effected through atrial and ventricular bipolar pace/sense electrode pairs at the ends of right atrial/superior vena cava (RA/SVC) and right ventricular (RV) leads 140 and 116, respectively, fixed in the right atrium 12 and right ventricle 16, respectively, that are electrically coupled to the circuitry of IPG 100 through a connector block 120. The coronary sinus (CS) lead 130 includes an elongated insulating lead body enclosing one elongated coiled wire conductor coupled to an elongated exposed coil wire CS cardioversion electrode 134. CS cardioversion electrode 134, illustrated in broken outline, is located within the coronary sinus and great vein 108 of the heart 102 and may be about 5 cm in length. At the proximal end of the CS lead 130 is a connector end 132 having an exposed connector coupled to the coiled wire conductor and attached within the connector block 120 to connector block terminals in a manner well known in the art.

The RA/SVC lead 140 includes an elongated insulating lead body carrying at least three concentric, electrically isolated, coiled wire conductors separated from one another by tubular insulating sheaths. The lead body is formed in a manner well known in the art in an atrial J-shape in order to position its distal end in the right atrial appendage. An atrial pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed coil, RA/SVC cardioversion electrode 150 is supported on RA lead 140 extending proximally to pace/sense ring electrode 144 and coupled to the third coiled wire conductor within the RA lead body. RA/SVC cardioversion electrode 150 preferably is 10 cm in length or greater and is configured to extend from within the SVC and toward the tricuspid valve 36. At the proximal end of the RA lead 140 is a bifurcated connector 142 which carries three exposed electrical connectors, each coupled to one of the coiled wire conductors, that are attached within the connector block 120 to connector block terminals in a manner well known in the art.

The delivery of atrial cardioversion/defibrillation therapies to the atria 12 and 14 may be effected through selected combinations of intracardiac electrodes, e.g. the illustrated exemplary RA/SVC cardioversion electrode 150 and the CS cardioversion electrode 134. The exposed surface of the outer housing or can of the IPG 100 is optionally used as can electrode 110 serving as a subcutaneous remote cardioversion electrode in combination with one or more intracardiac cardioversion electrode for cardioverting or defibrillating the atria. A remote, subcutaneous defibrillation patch electrode or epicardial patch electrode may be provided in addition to or substitution for the can electrode 110.

The RV lead 116 is depicted in a conventional configuration and includes an elongated insulating lead body, enclosing at least three concentric, electrically isolated, coiled wire conductors, separated from one another by tubular insulating sheaths. Located adjacent the distal end of the RV lead 116 are a pace/sense ring electrode 124, and a helical, pace/sense electrode 126, mounted retractably within an insulating electrode head 128. Helical electrode 126 is adapted to be extended out of the electrode head 128 and screwed into the ventricular apex in a manner well known in the art. RV pace/sense electrodes 124 and 126 are each coupled to a coiled wire conductor within the RV lead body and are employed for cardiac pacing in the ventricle and for sensing near-field R-waves. In the embodiments of the present invention devoted to delivering ventricular cardioversion therapies, the RV lead 116 also supports an elongated, exposed wire coil, cardioversion electrode 170 in a distal segment thereof adapted to be placed in the right ventricle 16 of heart 10 and connected to a further coiled wire conductor within the RV lead body. Although not specifically illustrated in FIG. 5, it will be understood that the ventricular cardioversion therapies may be delivered between further RV cardioversion electrode in combination with the intracardiac RV cardioversion electrode 170 or between the intracardiac ventricular cardioversion electrode and the IPG can electrode 110 and/or the CS cardioversion electrode 134 or the RA/SVC cardioversion electrode 150. At the proximal end of the RV lead 116 is a bifurcated connector end 118 having a plurality of electrical connectors, each coupled to one of the coiled conductors in the RV lead body, that are attached within the connector block 120 to connector block terminals in a manner well known in the art.

Certain embodiments of the present invention work more efficaciously with cardioversion electrodes substantially in contact with the heart chambers. Atrial or ventricular epicardial cardioversion electrodes may be used instead of one or more of the illustrated intracardiac cardioversion electrodes of FIG. 5 if they are flexible and do not interfere with the deflation or compression of the heart chamber. When the heart chambers are deflated on blood emptying or subjected to compression at end inspiration, the total impedance between the electrode pairs decreases. However, when one or more remote, subcutaneous patch or can electrode is employed, the total impedance between the electrode pairs may increase at the end inspiration point or phase due to the expansion of the chest and inflation of the lungs, increasing the distance between the cardioversion electrode pair. In this case, the optimum respiration point or phase for delivery of the cardioversion therapy in synchrony with the lowest atrial blood pressure may be at the end of the expiration point or phase or more preferably at the onset of inspiration. The end of expiration stage may optionally be extended by the patient holding his/her breath.

Turning to the determination of the deflation of the heart chamber in question at minimum atrial blood pressure during passive ventricular filing, at least one of the leads 116, 130 or 140 traversing the right atrium 12 or right ventricle 16 is fitted with an absolute pressure sensor of the type described in commonly assigned U.S. Pat. No. 5,535,752 issued Jul. 16, 1996 to Halperin et al. or U.S. Pat. No. 5,564,434 issued Oct. 15, 1996 to Meisel et al. For example, such a capacitive absolute pressure sensor (CAPS) 180 is for convenience shown on the RV lead 116 situated along its length so that it is positioned in the right atrium 12 or right ventricle. Associated lead conductors extend from the CAPS 180 to the RV lead connector 118 for connection with terminals within the connector block 120. The atrial blood pressure may be detected with the CAPS 180 located in the right atrium 12 as shown in FIG. 5 or alternatively may be detected with the CAPS 180 located in the right ventricle 16 if the detection and treatment is provided for ventricular tachycardia.

FIG. 6 is a functional schematic diagram of the circuitry of a dual chamber, implantable PCD IPG 100 in which the present invention may usefully be practiced. Certain of the pace/sense and cardioversion/defibrillation functions and associated leads and electrodes may be disabled or not provided to configure the PCD system to operate in accordance with the preferred embodiments and variations described below. In all such embodiments and variations, the atrial pacing capability may be eliminated. Therefore, FIG. 6 should be taken as exemplary of the circuitry of the type of single chamber or dual chamber PCD IPG 100 in which the invention may be embodied, and not as limiting, as it is believed that the invention may usefully be practiced in a wide variety of device implementations, as long as a pacing mode providing either bradycardia pacing or tachycardia pacing therapies is retained.

The PCD IPG circuitry of FIG. 6 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 6 depicts the atrial and ventricular pace/sense lead connector terminals 328, 330 and 326, 324, respectively, the atrial and ventricular cardioversion/defibrillation lead connector terminals 322, 320, the CAPS 180 connector terminals 340, 342 and the impedance lead 160 connector terminal 332, all within the connector block 120, and a hard wired connection with the can electrode 110.

The internal circuitry of the CAPS 180 may take the form described in the above referenced Meisel et al. patent and is adapted to be coupled to the atrial blood pressure signal processor 280 that may take the form described in the above-referenced 'Halperin et al. patent by means of the terminals 340 and 342. The blood pressure signal processor 280 powers the CAPS 180 and demodulates the pressure signal as the capacitance within CAPS 180 changes with pressure changes in the chamber in which the CAPS 180 is implanted. The atrial or ventricular blood pressure signal may be processed to provide an absolute blood pressure value and a rate of change or dP/dt value that is digitized in signal processor 280 and supplied to the microprocessor 224 for processing in accordance with the invention. In accordance with the embodiments of the invention, the blood pressure signal processor is enabled to develop the pressure signal when high rate atrial tachycardia or atrial fibrillation/flutter is confirmed in order to time the delivery of the cardioversion therapy to the atria 12, 14.

In one form of practicing the first embodiment of the invention, the physician can test the efficacy of the atrial blood pressure signal processor 280 in a patient work-up after or during the implantation of the CAPS 180 in the appropriate heart chamber. Using an external programmer in a manner known in the art, the physician can initiate the operation of the atrial blood pressure signal processor 280 and telemetry out of the atrial or ventricular blood pressure signal levels when the patient is in normal sinus rhythm and when a tachyarrhythmia episode is present. In the variation intended to treat atrial tachyarrhythmias, the physician may also program on ventricular pacing at a rate exceeding the intrinsic ventricular rate while conducting the test. Based on the observed atrial or ventricular blood pressure signal fluctuations and other observations of the opening and closing times of the heart valves, the physician may then program in blood pressure threshold signal levels to be maintained in RAM 226 as programmed values to be used in comparison with the measured blood pressure signal levels as described below. A self learning or adaptive program may alternatively be used to establish the blood pressure threshold levels or otherwise directly determine the minimum blood pressure signal level in the intrinsic or paced cardiac cycle.

In the following described examples of the second embodiment, a respiration signal detection mode is also initiated by microprocessor 224 when the tachyarrhythmia is initially detected at onset or is confirmed in order to time the delivery of the cardioversion therapy to the heart chamber. The switch network 280 is selectively operated by the microprocessor 224 to couple the can electrode 110 through conductor 344 to one input/output terminal of impedance signal processor 290 and to couple a further electrode selected from among the electrodes in the lead system in use through conductor 346 to the other input/output terminal of impedance signal processor 290. In the example depicted in FIG. 5, the separate impedance lead 160 and impedance electrode is provided in the lead system and is attached to terminal 332 in the block diagram of FIG. 6, However, another electrode could be selected in switch matrix 208, eliminating the need for the impedance lead 160.

Assuming the use of the separate impedance lead 160, when the impedance signal processor 290 is enabled by the microprocessor 224, it supplies a low energy, constant current signal to the spaced apart respiration electrodes 166 and 110 through the conductors 344 and 346 and enabled switches in switch network 208. The voltage across the input/output terminals of the impedance signal processor 290 changes as a function of the change in impedance of the current pathway across the patient's chest between the impedance electrode 166 and can electrode 110. The impedance change is a function of the change in distance in the current pathway within the chest and across the lungs 70, 72 and between the selected impedance electrodes 110 and 166 which increases with inspiration and decreases with expiration.

Such impedance signal deriving and processing techniques for use in the present invention are known in the prior art employed in other applications. For example, impedance plethysmography using separate impedance electrodes or pace/sense electrodes to derive a physiologic signal related to patient exercise that is processed to determine an optimum bradycardia pacing rate is disclosed in U.S. Pat. Nos. 4,702,253 and 4,697,591, incorporated herein by reference. An extensive discussion of prior art impedance measuring systems, electrodes, and techniques for a variety of medical device uses is set forth in U.S. Pat. No. 5,179,946, incorporated herein by reference. In the '946 patent and U.S. Pat. No. 5,385,576, the cardiac impedance including the blood impedance in the heart chambers is used to determine or classify tachyarrhythmias that result in hemodynamic compromise, and the fluctuations of the impedance signal due to reparation are ignored or filtered out.

By contrast, in the present invention, the magnitude and frequency of the change of the impedance signal corresponding to the tidal volume and the respiration rate are employed to determine the optimum reduction in interelectrode impedance in the path between the particular set of cardioversion electrodes. The minor fluctuations in the impedance signal due to cardiac function are ignored, although they may be employed in substitution for or in conjunction with the atrial blood pressure signal to determine the minimum atrial blood pressure during the cardiac cycle. In either case, the measurement of the change in impedance as reflected by an increase in the voltage signal can be used as one method for determining when inspiration begins and reaches end inspiration in the respiratory cycle. As inspiration begins, the chest swells, decreasing the size of the pleural cavity and compressing the atria 12, 14. At the same time, the respiration cycle has an influence on the autonomic nerves as shown in FIG. 4. The sympathetic nerve activity increasing during inspiration may lead to increased excitability of atrial cells and lower the energy required to cardiovert the atria. Moreover, it is postulated in accordance with the invention that the increase in pleural impedance may also act to insulate the heart so that the atrial or ventricular cardioversion energy delivered directly to the heart through intracardiac and/or epicardial electrodes is concentrated within the atria or ventricles, respectively.

In one form of practicing the second embodiment of the invention, the physician can test the efficacy of the respiration detection system in a patient work-up after or during the implantation of the system. Using an external programmer in a manner known in the art, the physician can initiate the operation of the respiration signal processor and telemetry out of the impedance signal levels as the patient breathes and is instruct to hold his/her breath at end inspiration and end expiration. Based on the observed impedance fluctuations, the physician may then program in respiration threshold signal levels to be maintained in RAM 226 as programmed values to be used in comparison with the measured impedance signal levels as described below. A self learning or adaptive program may alternatively be used to establish the threshold levels or otherwise directly determine the end inspiration and end expiration point or phase.

Returning to FIG. 6 and assuming that the system is configured to respond to atrial tachyarrhythmias and to deliver cardioversion therapies to the atria, terminal 322 is adapted to be coupled through RA lead 140 to RA/SVC electrode 150 and terminal 320 is adapted to be coupled through CS lead 130 to CS cardioversion electrode 134. Terminals 322, 320 and, alternatively, can electrode 110 are coupled to high voltage (HV) output circuit 234 which includes high voltage switches controlled by CV/DEFIB CONTROL logic 230 via control bus 238. The switches within HV output circuit 234 control which cardioversion electrodes are employed and which are coupled to the positive and negative terminals of the capacitor bank including capacitors 246 and 248 during delivery of intermediate and high voltage cardioversion and defibrillation shocks.

Terminals 324 and 326 of the connector block are adapted to be coupled through RV lead 116 to RV pace/sense electrodes 124 and 126 for sensing and pacing in the ventricle. Terminals 328 and 330 are adapted to be coupled through RA/SVC lead 140 to RA pace/sense electrodes 144 and 146 for sensing and pacing in the atrium. Terminals 324 and 326 are coupled to the inputs of Ventricular sense amplifier 200 through switches in switch network 208. Ventricular sense amplifier 200 which preferably takes the form of an automatic gain controlled amplifier providing an adjustable sensing threshold as a function of the measured R-wave signal amplitude. A VSENSE signal is generated on R-OUT line 202 whenever the signal sensed between electrodes 124 and 126 exceeds the current ventricular sensing threshold. Terminals 328 and 330 are coupled to the Atrial sense amplifier 204 through switches in switch network 208. Atrial sense amplifier 204 preferably also takes the form of an automatic gain controlled amplifier providing an adjustable sensing threshold as a function of the measured P-wave amplitude. An ASENSE signal is generated on P-OUT line 206 whenever the signal sensed between pace/sense electrodes coupled to terminals 328, 330 exceeds the current atrial sensing threshold. The A-PACE and V-PACE output circuits 214 and 216 are also coupled to terminals 328, 330 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the ventricular and atrial sense amplifiers 200 and 204 may correspond to that disclosed in U.S. Pat. No. 5,117,824, incorporated herein by reference in its entirety.

Switch matrix 208 is also used in an EGM sensing mode to select which of the available pace/sense electrodes (or cardioversion electrodes) are coupled to the inputs of wide band (0.5–200 Hz) EGM sense amplifier 210 for use in digital signal storage and analysis of the patient's atrial and ventricular EGM. Therefore, the terminals 328, 330, adapted to be coupled to the atrial pace/sense electrodes 144, 146, and the terminals 324, 326, adapted to be coupled to the ventricular pace/sense electrodes 124, 126, are also coupled to the switch matrix 208. Switches within switch matrix 208 are selectively controlled by the microprocessor 224 or circuits within the pacer timing and control circuitry 212, via data/address bus 218, to couple the terminals 328, 330 or 324, 326 to the inputs of band pass amplifier 210 and to thereby apply atrial or ventricular signals to the band pass amplifier 210. Output signals from band pass amplifier 210, in response to the applied atrial or ventricular signals, are provided to multiplexer 220, and thereafter converted to multi-bit digital signals by A/D converter 222, for storage in RAM in ROM/RAM 226 under control of DMA 228. Microprocessor 224 may employ digital signal and morphology analysis techniques to characterize the digitized signals stored in ROM/RAM 226 to recognize and classify the patient's heart rhythm employing any of the numerous signal processing methodologies known to the art.

The PCD IPG circuitry of FIG. 6 provides atrial and/or ventricular cardiac pacing for bradycardia and tachycardia conditions and atrial synchronized cardioversion/defibrillation therapies atrial fibrillation/flutter in accordance with the timing algorithms described below and therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200.

In normal pacing modes of operation, intervals defined by pacer timing and control circuitry 212 include atrial and ventricular pacing escape intervals, blanking intervals, refractory periods and pulse widths of pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the atrial and ventricular escape interval counters within pacer timing and control circuitry 212 are reset upon non-refractory ASENSE and VSENSE events on lines 202 and 206. In accordance with the selected pacing mode, pacer timing and control circuitry 212 provides pace trigger signals to the A-PACE and V-PACE output circuits 214 and 216 on time-out of the appropriate escape interval counters to trigger generation of atrial and/or ventricular pacing pulses. The pacing escape interval counters are also reset on generation of pacing pulses, and thereby control the basic timing of cardiac pacing functions.

Microprocessor 224 operates as an interrupt driven device responsive to interrupts from pacer timing and control circuitry 212 corresponding to the ASENSE and VSENSE events and provided via data/address bus 218. Any necessary mathematical calculations to be performed by microprocessor 224 and any updating of the values or intervals controlled by pacer timing/control circuitry 212 take place following such interrupts.

For example, in response to a VSENSE, the V-V interval separating that VSENSE from the most recent VSENSE or V-PACE or the P-R interval separating that VSENSE from an immediately preceding ASENSE or P-PACE may be stored temporarily in memory. Similarly, in response to an ASENSE, the A-A interval separating that ASENSE from the most recent preceding ASENSE or A-PACE or the V-A interval separating that ASENSE from the immediately preceding VSENSE or R-PACE may be stored temporarily in memory. Preferably, a portion of RAM in the ROM/RAM 226 (FIG. 6) is configured as a plurality of recirculating buffers, capable of holding a preceding series of such measured intervals, which may be analyzed to determine whether the patient's heart is presently exhibiting atrial or ventricular tachyarrhythmia, and, in the context of the atrial system, whether a ventricular rhythm is present and regular enough to be employed in timing the delivery of the atrial cardioversion therapy as described below.

In the atrial cardioversion context, pacer timing and control circuitry 212 determines the presence of a high rate atrial (or ventricular) tachycardia or atrial fibrillation/flutter from timing and regularity of the stored A-A intervals in a manner well known in the art. For example, presence of atrial tachyarrhythmia may be confirmed by means of detection of a sustained series of short A-A intervals of an average rate indicative of tachyarrhythmia or an unbroken series of a certain number of successive short A-A intervals. The suddenness of onset of the detected high rate, the stability of the high rate, or a number of other factors known to the art may also be measured at this time. The comparative V-V intervals as well as the absence or diminution of the atrial blood pressure wave fluctuation in synchrony with ASENSE events may also be employed in confirming the presence of the atrial tachyarrhythmia.

In the event that an atrial tachyarrhythmia is detected and confirmed, and an initial anti-tachyarrhythmia pacing regimen is prescribed, appropriate timing intervals for controlling generation of anti-tachyarrhythmia pacing therapies are loaded from microprocessor 224 into the pacer timing and control circuitry 212. The timed or burst pacing therapies are delivered by the A-PACE pulse generator 214 to the atrial pace/sense electrodes in a manner well known in the art. In accordance with one aspect of the present invention, the timing of delivery of Such anti-tachyarrhythmia pacing therapies may also be governed by the algorithms described below in the context of delivering a cardioversion shock therapy.

In response to the detection of atrial (or ventricular) fibrillation or tachyarrhythmia requiring a cardioversion shock therapy, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, and the monitored voltage signal is passed through multiplexer 220, digitized, and compared to a predetermined value set by microprocessor 224 in ADC/comparator 222. When the voltage comparison is satisfied, a logic signal on Cap Full (C.F.) line 254 is applied to cardioversion/defibrillation control circuit 230, terminating charging. Thereafter, timing of the delivery of the defibrillation or cardioversion shock is controlled by pacer timing/control circuitry 212 in response to commands from the microprocessor 254 operating in accordance with the preferred embodiments of the invention as described in detail below. Following delivery of the cardioversion shock therapy, the microprocessor 224 then returns the operating mode to cardiac pacing and awaits the next successive interrupt due to pacing or the occurrence of a sensed atrial or ventricular depolarization.

In the illustrated IPG circuit of FIG. 6, delivery of the cardioversion shocks is accomplished by output circuit 234, under control of control circuitry 230 via control bus 238. Output circuit 234 determines whether a monophasic or biphasic shock is delivered, the polarity of the cardioversion electrodes and which cardioversion electrodes are involved in delivery of the shock or shocks. Output circuit 234 also includes high voltage switches which control whether cardioversion electrodes are coupled together during delivery of the shock. Alternatively, cardioversion electrodes intended to be coupled together during the shock may simply be permanently coupled to one another, either exterior to or interior of the device housing, and polarity may similarly be pre-set, as in current ICDs and PCDs. An example of output circuitry for delivery of biphasic shock regimens to multiple electrode systems may be found in U.S. Pat. No. 4,727,877, incorporated by reference in its entirety.

The particular cardioversion therapies are programmed in during a patient work up by the physician, and a menu of therapies is typically provided. For example, on initial detection of an atrial (or ventricular) tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial fibrillation is identified, the typical therapy will be delivery of a high amplitude cardioversion shock, typically up to 4.0 Joules. It is envisioned that the amplitude of the cardioversion shock may be incremented in response to failure of an initial shock energy to terminate the tachyarrhythmia.

A number of embodiments and variations of algorithms for implementing the timing of the delivery of the atrial cardioversion therapies are set forth in the following discussion. It will be understood that these algorithms may be implemented in the PCD IPG as one or more of a series of therapies that may be delivered in a programmable regimen in response to a tachyarrhythmia episode. Further, more aggressive, therapies may be invoked upon failure of a given therapy to achieve cardioversion.

Figure 7:
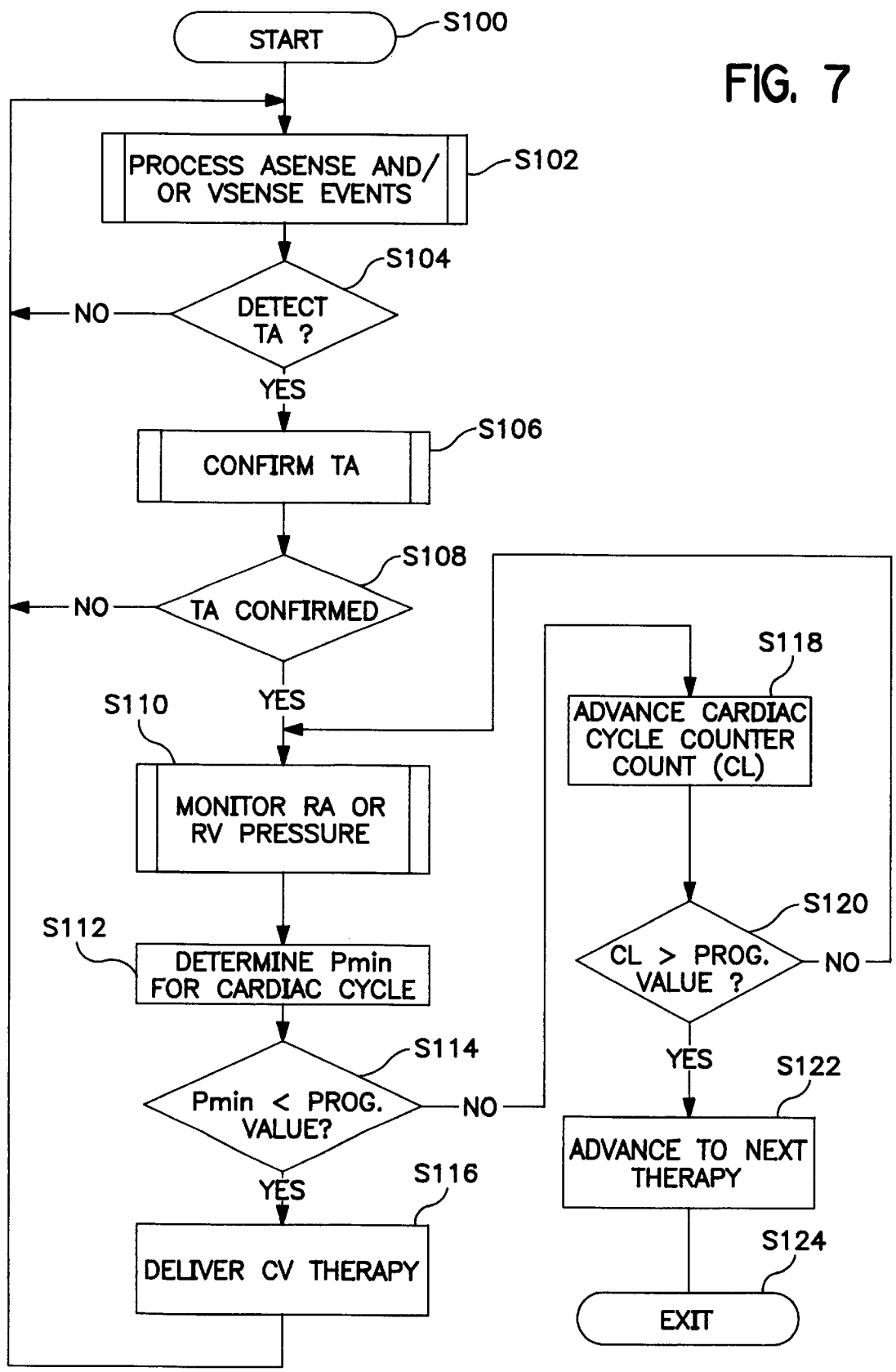
FIG. 7 is a flow chart of the operation of components of the system of FIGS. 5 and 6 in a first embodiment timing delivery of the atrial cardioversion therapy to the lowest measured atrial or ventricular blood pressure level following, a sensed intrinsic ventricular event.

FIG. 7 is a flow chart of the operation of a system formed of components of the PCD IPG and lead system of FIGS. 5 and 6 in accordance with the first embodiment of the invention in the context of treating either an atrial tachyarrhythmia of the types described above. In this illustration of the first embodiment, the reduction in volume and the relaxation of the heart chambers that occurs in the passive filling phase as evidenced by measured atrial or ventricular blood pressure signal characteristics and, is used to time delivery of an cardioversion therapy to the atria. If the relaxation phase cannot be determined from the blood pressure signal over a number of heart cycles or within a programmed time period, then the next therapy is delivered, which may be the same therapy, but without synchronization to the minimum blood pressure level.

In step S102, the ASENSE and VSENSE events and other parameters are monitored and processed from which the existence of a tachyarrhythmia (TA) can be determined. In steps S104–S108, the presence of a tachyarrhythmia of the types described above is detected and confirmed employing the above-described conventional methods. In step S110, the blood pressure signals from the blood pressure signal processor 280 are monitored over one or more following cardiac cycles. The blood pressure signal is continuously sampled, and sample values are compared over the V-V cardiac cycle (determined by the detection of successive VSENSE events or V-PACE events) by the blood pressure signal processor 280 to detect the minimum blood pressure $P_{min}$ during the cycle. $P_{min}$ may optionally be compared to a desired threshold value at S114 and the cardioversion therapy is delivered in step S116 when and if $P_{min}$ is equal to or less than the programmed value, provided that the minimum pressure occurs outside the vulnerable period of the ventricles. Alternatively the cardioversion/defibrillation therapy may be delivered synchronized to $P_{min}$ regardless of its value, by omitting step S114 and proceeding directly to step S116. Step S116 should be understood to include additional criteria for shock delivery relative to sensed ventricular events to assure that the cardioversion/defibrillation shocks are delivered outside the vulnerable period of the ventricles. Delivery of atrial cardioversion/defibrillation shocks should be limited to delivery of the cardioversion pulses timed closely enough to a ventricular depolarization to occur before the vulnerable period as in U.S. Pat. No. 5,584,864 issued to White, incorporated herein by reference in its entirety or following a defined period initiated on the ventricular depolarization so that the pulse occurs after the ventricular vulnerable period as disclosed in U.S. Pat. No. 5,411,524, issued to Mehra, also incorporated herein by reference in its entirety. It should be noted that the minimum blood pressure in the atria and ventricles generally occurs after the ventricular vulnerable period following a ventricular depolarization. Thus, in most cases, defining a minimum safety delay period following a paced or sensed ventricular depolarization which must elapse prior to delivery of the atrial cardioversion/defibrillation pulse will be the preferred approach, and in most cases this safety delay period will elapse prior to the detected pressure minimum, allowing synchronization to the detected minimum pressure. However, if the safety delay period has not elapsed when the pressure minimum is detected, the cardioversion pulse should be delayed to allow the safety delay period to expire.

Steps S100–S116 represent the simplest preferred first embodiment of the invention in respect to timing the delivery of cardioversion/defibrillation therapies in synchrony with the minimum blood pressure signal $P_{min}$ in and assumes that the V-V cardiac rhythm is organized sufficiently enough to demonstrate blood pressure signal level fluctuations between maximum and minimum signal levels. The simple algorithm may be augmented in steps S118–S122 to account for the situation where it is not possible to determine the minimum atrial blood pressure signal level $P_{min}$ during a succession of V-V intervals which is less than the threshold value. One approach would be to time-out a maximum therapy delivery time interval from the onset of the particular episode to terminate the attempt to time delivery to the minimum blood pressure and invoke a more aggressive or back-up therapy.

In the preferred embodiment of FIG. 7, a ventricular cardiac cycle counter is incremented in step S118 whenever it is not possible to determine the minimum blood pressure signal $P_{min}$, and the count CL of the cardiac cycle counter is compared to a further programmable value in step S120. The cardiac cycle counter allows a programmed number of V-V cardiac cycles during which successive blood pressure signal measurements take place in steps S110–S114. If the cardiac cycle counter count CL equals or exceeds a maximum count in step S120, a further cardioversion therapy is selected in step S122 or the prescribed cardioversion therapy is delivered without attempting to synchronize delivery to the minimum blood pressure. Alternatively, the thresholds for determining the minimum blood pressure value may be changed and the process of steps S102–S122 repeated.

The operating algorithm of FIG. 7 is particularly applicable to the timing of delivery of cardioversion therapies in response to atrial fibrillation/flutter or to either atrial or ventricular high rate tachycardias where a desired minimum blood pressure signal level can be detected at the prevailing intrinsic ventricular rate. When only an atrial tachyarrhythmia is diagnosed, it is frequently accompanied by an intrinsic ventricular rate that is relatively lower and relatively regular so that the passive atrial emptying in the V-V cardiac cycle takes place, thereby lowering the blood pressure and allowing the atria to deflate.

Figure 8:
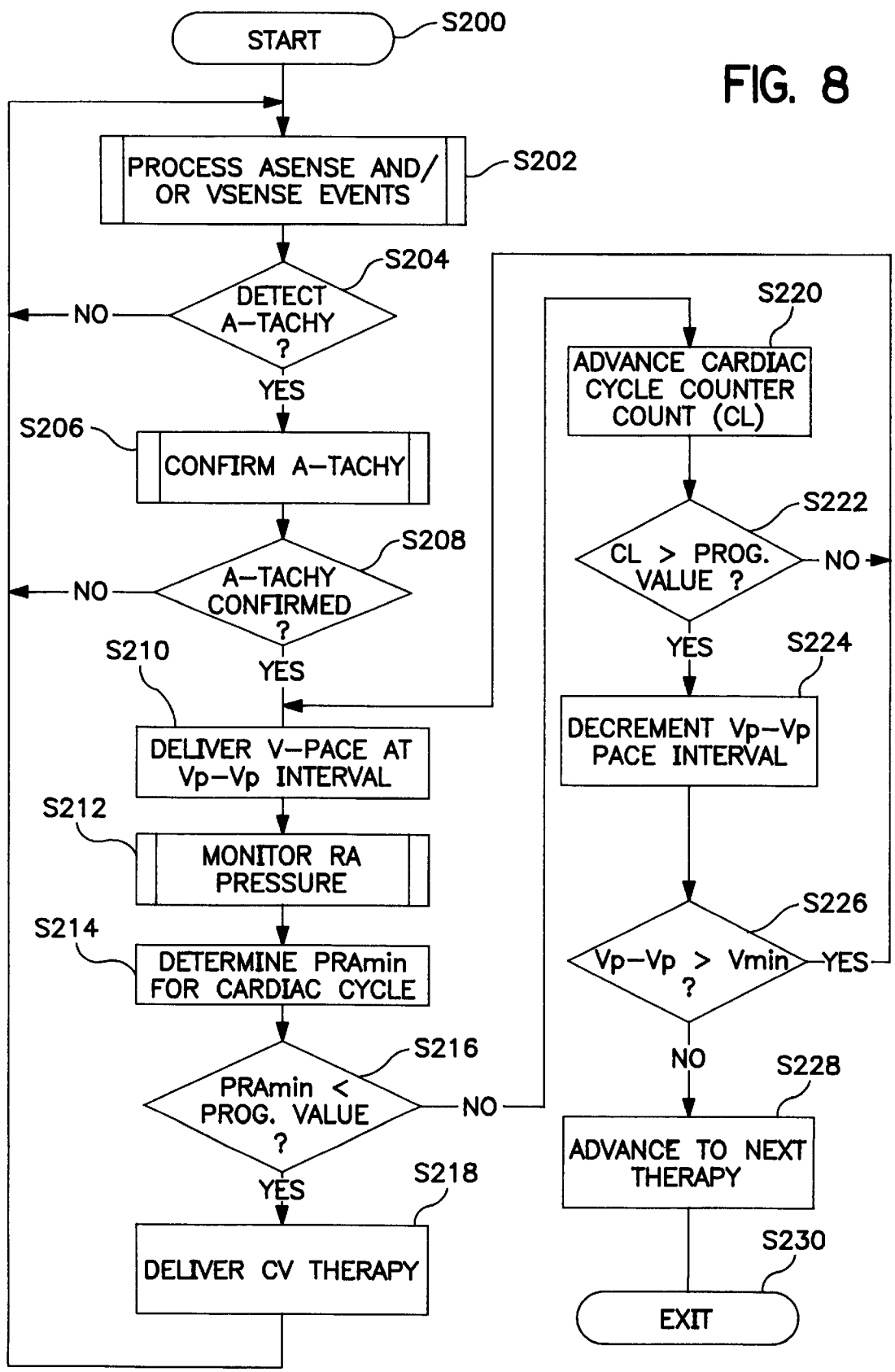
FIG. 8 is a flow chart of the operation of components of the system of FIGS. 5 and 6 in a variation of the first embodiment timing delivery of the atrial cardioversion therapy to the lowest measured atrial or ventricular blood pressure level following in a paced ventricular event.

The flow charts of FIG. 8 et seq. all disclose devices which employ atrial pressure sensors. It should be understood that in these devices a ventricular pressure sensor could be substituted, as discussed above.

FIG. 8 is a flow chart of the operation of the system of FIGS. 5 and 6 in a variation particularly usable in response to an atrial tachyarrhythmia. In this case, ventricular pacing is provided through the ventricular pace/sense electrodes 124, 126 at a $V_P$-$V_P$ pacing rate exceeding the intrinsic ventricular heart rate. Steps S200–S208 track the steps S100–S108 in the detection and confirmation of the A-TACHY episode, and ventricular pacing is initiated in step S210. Then, the minimum right atrial blood pressure $P^{RA}_{min}$ is measured and compared to a threshold value in steps S212–S216 in the manner of steps S110–S114 of FIG. 7. The therapy is delivered in step S218 as in step S116.

In steps S220 and S226, the ventricular pacing rate $V_P$-$V_P$ is varied if it is not possible to detect the desired minimum right atrial blood pressure signal $P^{RA}_{min}$ in step S216 after a number of attempts established by the cardiac cycle counter in steps S220 and S222. The right atrial pressure $P^{RA}$ is monitored to determine if an optimum relation between pacing rate and the minimum right atrial blood pressure signal $P^{RA}_{min}$ results in a desired minimum right atrial blood pressure signal that equals or falls below the programmed value in step S216. The ventricular pacing escape interval $V_P$-$V_P$ is decremented (pacing rate increased) in step S226, and the monitoring of the right atrial pressure continues in step S212 if the decremented escape interval does not equal or fall below a further minimum escape interval in step S226. The pacing interval is decremented until either a desirably low value of $P^{RA}_{min}$ occurs or the pacing rate reaches its programmed maximum value. If the desire value of $P^{RA}_{min}$ cannot be obtained, the device proceeds to the next programmed therapy at S228, as in S122 in FIG. 7.

It should be noted that the embodiments of FIGS. 7 and 8 may be practiced efficaciously with any combination of intracardiac and epicardial cardioversion electrodes substantially in contact with the heart chamber in question as well as with a remote, subcutaneous, cardioversion electrode of the types described above and disclosed in the prior art. When one or more subcutaneous electrodes are employed in the system, the decrease in inter-electrode impedance at the time that the heart chamber is emptying and relatively deflated can still be beneficial.

Figure 9:
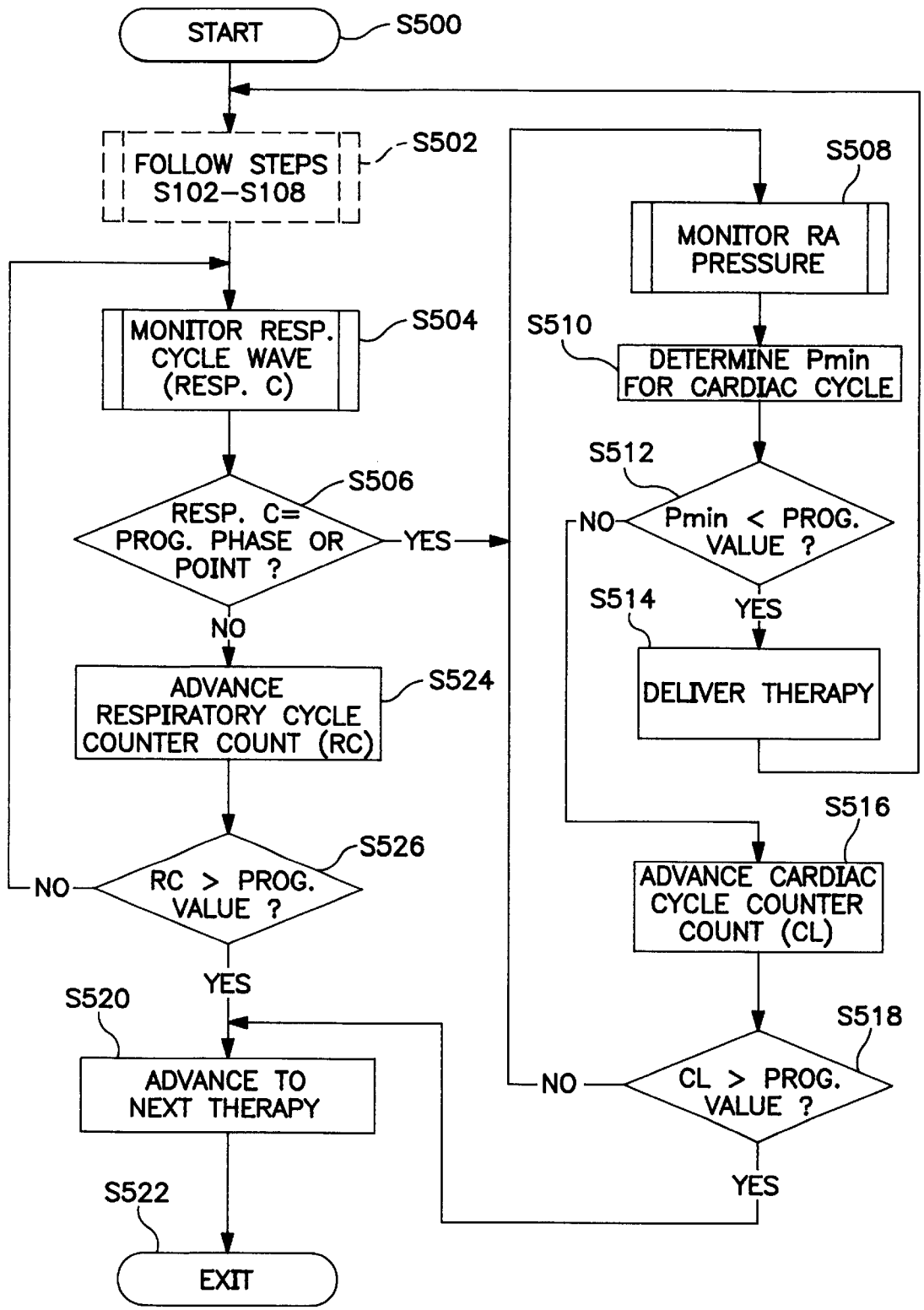
FIG. 9 is a flow chart of the operation of components of the system of FIGS. 5 and 6 in a second embodiment timing the delivery of the cardioversion therapy to the lowest measured atrial or ventricular blood pressure level following a sensed intrinsic ventricular event and during a programmed point or phase of the respiratory cycle.

Turning to FIG. 9, it is a flow chart of the steps of the second embodiment of the invention employing components of the PCD IPG and lead system of FIGS. 5 and 6 timing delivery of the cardioversion therapy to both a minimum atrial blood pressure signal level and to a point or phase of the respiratory cycle, particularly usable in atrial cardioversion in recognition that the volume and the autonomic tone of the atria for sustenance of atrial fibrillation/flutter are also influenced by the respiratory cycle. At step S502, the existence of the tachyarrhythmia is determined following steps S102–S108. The fluctuation of the respiratory cycle is preferably determined in step S504 by enabling the respiration signal processor 290 and the switch network 208 (or by enabling an equivalent system for monitoring the respiratory cycle). The start and end of the inspiration and expiration phases or other selected attributes of the respiration cycle are determined in step S504 from the impedance (voltage) signal amplitude or rate of change or other measured parameter. As explained above, the optimum point or phase of the respiratory cycle may be the end of inspiration or the end of expiration/beginning of inspiration, depending on the selection of cardioversion electrodes implanted in the or around the patient's heart, and is programmed into the IPG memory as either the maximum or minimum impedance (voltage) signal level. At step S504, the impedance waveform is sampled, and the peak or minimum signal level is determined in a manner similar to the manner of determining the minimum atrial blood pressure signal as described above in step S506. The programmed point is achieved when the maximum or minimum respiration signal amplitude is determined, and the programmed phase may constitute an indefinite continuation of the point due to a voluntary holding of the breath or absence of breathing.

In the case where the cardioversion therapy is a cardioversion shock, it may take several seconds for the high voltage output capacitors to charge to the programmed voltage. The monitoring of the respiratory cycle commences in step S310 during the charging time, but the determination of the programmed phase or point of the respiratory cycle in step S310 is delayed until confirmation is received on C.F. line 254.

When the programmed phase or point is determined in step S506, the minimum atrial blood pressure determination is made in steps S508–S522, and a cardioversion therapy is delivered following the steps S110–S124 of FIG. 7, described above. Steps S500–S514 constitute the simplest operating mode in the practice of the second embodiment of the invention, and steps S516–S522 may be used for the reasons described above with respect to FIG. 7.

In a variation of this embodiment, it will be assumed that the determination made in step S506 involves a comparison of the measured and sampled respiration impedance signal to programmed threshold minimum or maximum values. If, as a result of the comparison, the programmed point or phase cannot be determined in step S506 in a first respiration cycle, then a respiration cycle counter count (RC) is incremented in step S524. The incremented RC is compared to a programmed Count value in step S526, and if a number of respiratory cycles are completed without a successful determination of the programmed point or phase, then the back-up cardioversion therapy is delivered in step S520. The back-up therapy in this case may constitute turning to steps S508–S514 or S508–S522, i.e., abandoning the attempt to synchronize the delivery of the cardioversion therapy to the respiration cycle and resorting directly to attempting to synchronize the delivery to the atrial blood pressure minimum value.

Figure 10:
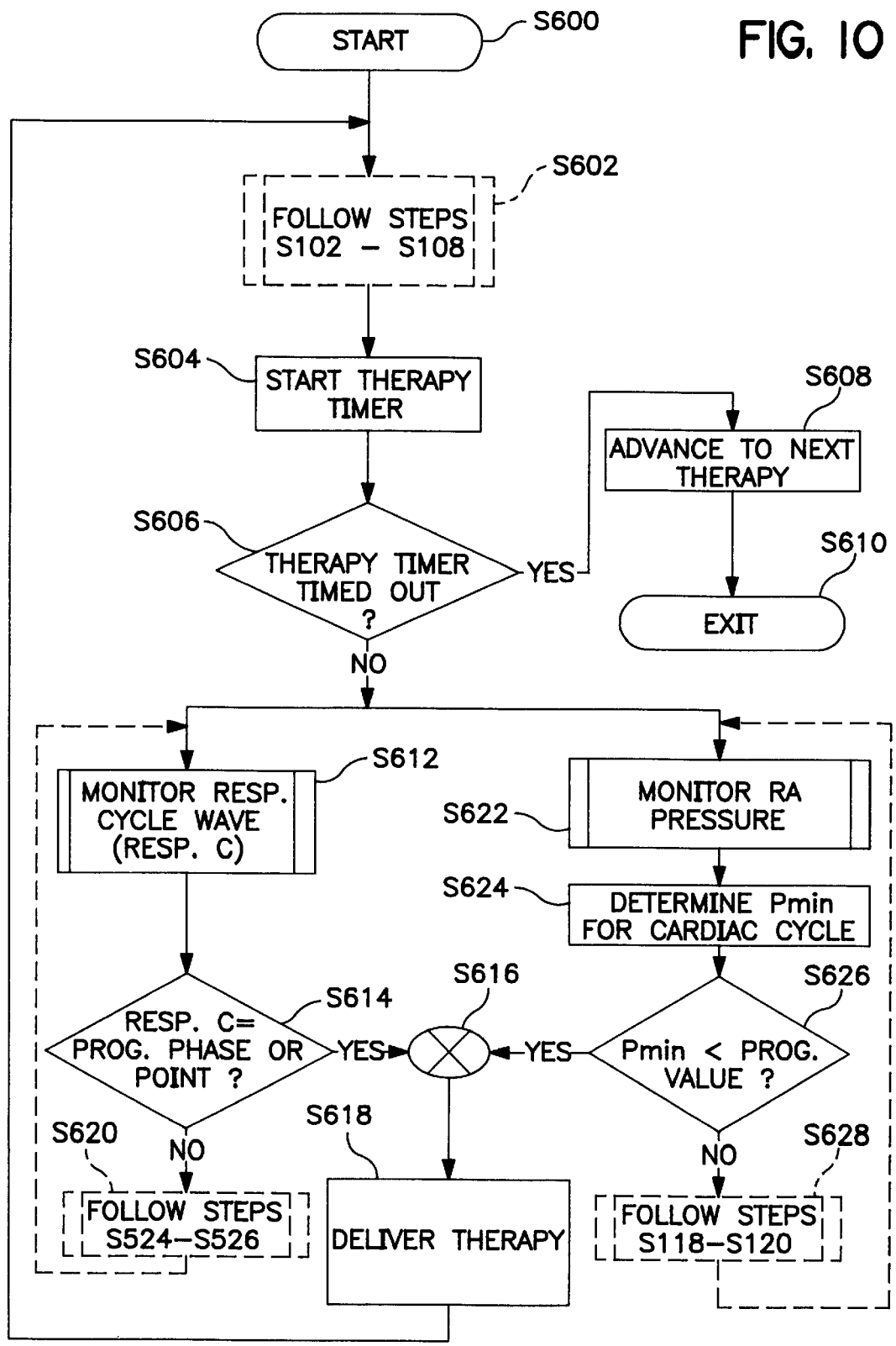
FIG. 10 is a flow chart of the operation of components of the system of FIGS. 5 and 6 in a variation of the second embodiment timing the delivery of the cardioversion therapy to the lowest measured atrial or ventricular blood pressure level following a sensed intrinsic ventricular event and during a programmed phase of the respiratory cycle in parallel operating steps and during time-out of a therapy timer.

Turning to FIG. 10, it depicts a flow chart of the operation of components of the system of FIGS. 5 and 6 in a variation of the second embodiment timing the delivery of the cardioversion therapy to the lowest measured atrial blood pressure level following a sensed intrinsic ventricular event and during a programmed phase of the respiratory cycle in parallel operating steps and during time-out of a therapy timer. A therapy timer function is defined by the microprocessor 224 to ensure that no more than a maximum delay period elapses from the detection and confirmation of the tachyarrhythmia and the delivery of the cardioversion therapy, thereby abandoning the attempt to synchronize the delivery of the cardioversion therapy to the programmed phase or point of the respiratory cycle and/or the minimum atrial blood pressure in the heart chamber.

The tachyarrhythmia is detected and confirmed following steps S102–S108 in step S602, and the therapy timer is started in step S604. Again, if a cardioversion shock therapy is programmed, the charging of the high voltage output capacitors is also commenced, and the remaining steps may not be completed until the high voltage capacitors are charged to the programmed voltage level. The therapy timer is monitored throughout all the steps, and if it times out in step S606, the next therapy is delivered in step S608 and the operation is completed in step S610. Steps S604–S610 may be incorporated into the operating methods of FIGS. 7–9 to place a time limit on the time spent in delivering the cardioversion therapy. In the method illustrated in FIG. 10, the steps S612–S614 of synchronizing the delivery of the cardioversion therapy to the programmed phase or point of the respiratory cycle for the particular cardioversion electrode configuration and the steps S622–S626 of synchronizing the delivery of the cardioversion therapy to the minimum atrial blood pressure are conducted in parallel operations. When both conditions are present, in step S616, the cardioversion therapy is delivered outside the ventricular vulnerable period at S618 and the therapy timer is turned off or reset. Optionally, the step S620, following the above-described steps S508–S512, is included and followed whenever it is not possible to determine the programmed phase or point of the respiratory cycle. Similarly, the step S626, following the above-described steps S118–S122, is included and followed whenever it is not possible to determine the minimum atrial blood pressure signal level $P_{min}$ in a V-V cardiac cycle. All of the parallel operations are halted on the time-out of the therapy timer in step S606.

Figure 11:
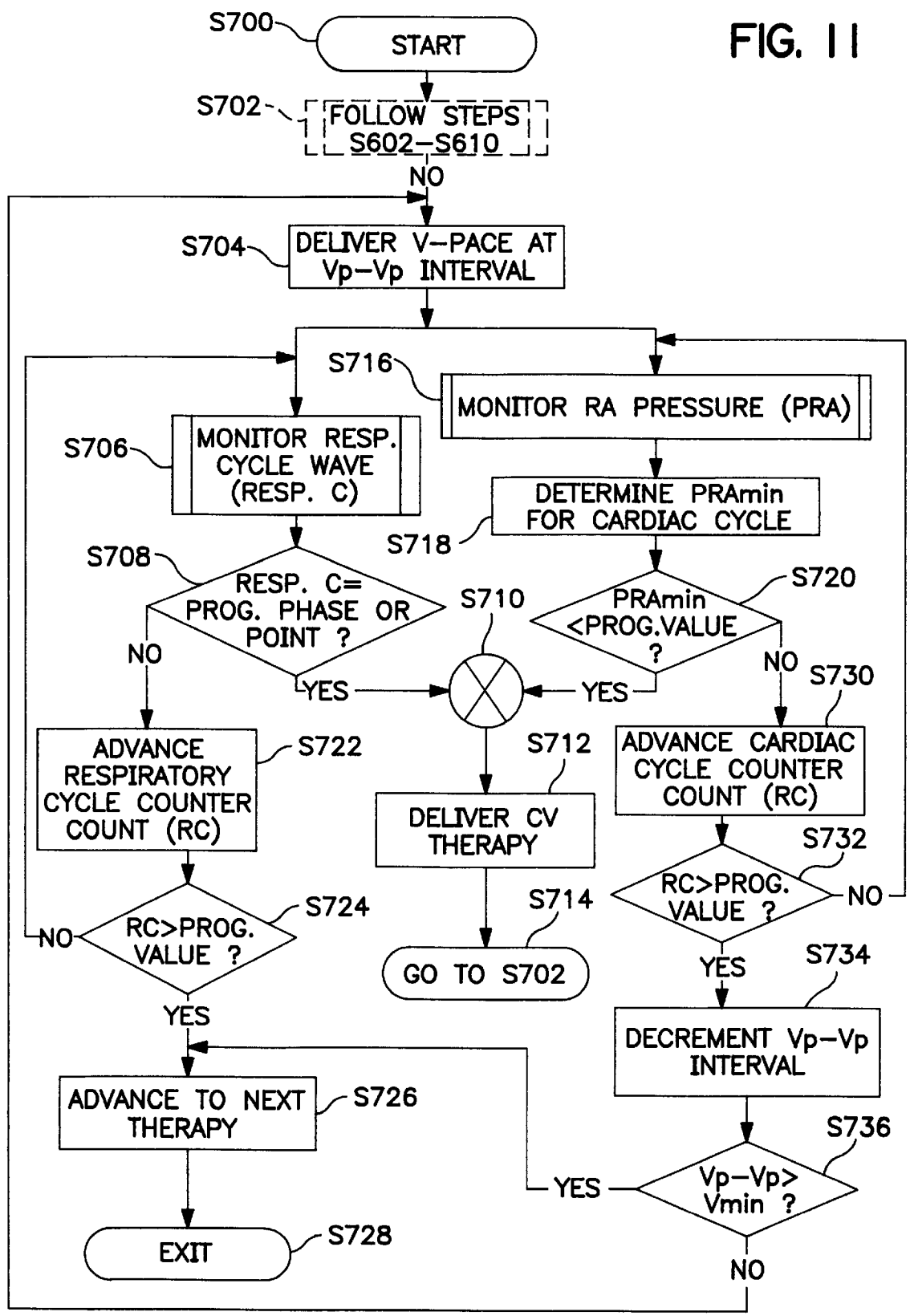
FIG. 11 is a flow chart of the operation of components of the system of FIGS. 5 and 6 in a further variation of the second embodiment timing the delivery of the cardioversion therapy to the lowest measured atrial or ventricular blood pressure level following a paced ventricular event and during a programmed phase of the respiratory cycle in parallel operating steps and during time-out of a therapy timer.

FIG. 11 is a flow chart of the operation of components of the system of FIGS. 5 and 6 in a further variation of the second embodiment timing the delivery of the cardioversion therapy to the lowest measured atrial blood pressure level following a paced ventricular event and during a programmed phase of the respiratory cycle in parallel operating steps and during time-out of the therapy timer. This variation of the second embodiment assumes that atrial tachyarrhythmia is detected and confirmed and the therapy timer is started in steps S702, following steps S602–S610, and that ventricular pacing is necessary in step S704 to stabilize the cardiac cycle. In the method illustrated in FIG. 11, the steps S706–S708 of synchronizing the delivery of the cardioversion therapy to the programmed phase or point of the respiratory cycle for the particular cardioversion electrode configuration and the steps S716–S720 of synchronizing the delivery of the cardioversion therapy to the minimum atrial blood pressure are also conducted in parallel operations. When both conditions are present, in step S710, the cardioversion therapy is delivered outside the ventricular vulnerable period and the therapy timer is turned off or reset in step S712.

Optionally, the steps S722 and S724 are provided for limiting the number of attempts to determine the programmed phase or point of the respiratory cycle in step S708 before resorting to delivery of the next or back-up therapy in step S726. Steps S730–S7736 decrement the $V_P$-$V_P$ pacing escape interval and limit the number of attempts to determine the minimum atrial blood pressure and synchronize delivery of the cardioversion therapy to it before also resorting to the delivery of the back-up therapy in step S726.

It will be understood that in each such embodiment, staged therapies of increasing energy level may be provided by programming of the IPG operating mode. If the applied therapy is not successful, then a higher energy therapy may be provided. In commercial implementations, the invention nay be embodied as part of an implantable PCD system, particularly for providing cardioversion therapies, of the types disclosed in commonly assigned U.S. Pat. Nos. 5,165,403, 5,292,338 or 5,314,430 employing two or more cardioversion electrodes arrayed in operative relation to the chamber of the heart. Alternatively, the present invention may be employed as part of an implantable arrhythmia control device including or substituting other cardioversion therapies of the types described above in pre-treatment of the chamber or substitution for the cardioversion shock therapy. The present invention is directed to the timing of the delivery of such cardioversion therapies, rather than the type of therapy, such that it is delivered when an optimum point or phase of the respiratory cycle is achieved for the particular cardioversion electrode configuration for delivering cardioversion therapies to the chamber, such that the chamber is most receptive to being converted to normal sinus rhythm.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A method of effecting cardioversion between cardioversion electrodes implanted in a patient's body comprising the steps of:

detecting a tachyarrhythmia of a heart chamber;
   measuring intracardiac blood pressure during a cardiac cycle for deriving a measured blood pressure value;
   determining a minimum blood pressure level in the heart; and
   delivering a cardioversion therapy across the cardioversion electrodes timed to substantially coincide with the minimum blood pressure level.

2. The method of claim 1 wherein the step of determining a minimum blood pressure level further comprises the steps of:

providing a programmable blood pressure threshold value; and
   comparing the measured blood pressure value to the programmable threshold value and providing the minimum blood pressure level when the measured blood pressure value falls below the threshold value.

3. The method of claim 1 wherein the delivering step further comprising the steps of:

detecting ventricular depolarizations and providing ventricular sense event signals in response thereto;
   timing a ventricular safety delay from the ventricular sense event signal to ensure that the ventricular vulnerable period is elapsed at the end of the ventricular safety delay; and
   delaying the delivery of the cardioversion therapy until the time-out of the ventricular safety delay, if necessary.

4. The method of claim 1 further comprising the steps of:

detecting ventricular depolarizations and providing ventricular sense event signals in response thereto;
   determining a ventricular cardiac cycle from successive ventricular sense event signals;
   incrementing the count of a cardiac cycle counter at the end of a ventricular cardiac cycle in response to a comparison during the cardiac cycle that does not provide a minimum blood pressure value during a cardiac cycle; and
   providing a back-up cardioversion therapy to the patient's heart chamber in response to a predetermined count of the cardiac cycle counter.

5. A method of effecting atrial cardioversion between atrial cardioversion electrodes implanted in relation to the atria of a patient's heart comprising the steps of:

detecting an atrial tachyarrhythmia;
   measuring intracardiac blood pressure during a cardiac cycle for deriving a measured blood pressure value;
   determining a minimum blood pressure during the cardiac cycle; and
   delivering a cardioversion therapy across the atrial cardioversion electrodes timed to substantially coincide with the minimum blood pressure level.

6. The method of claim 5 further comprising the steps of:

detecting atrial depolarizations of the heart and providing atrial sense event signals;
   detecting ventricular depolarizations of the heart and providing ventricular sense event signals; and
   pacing the ventricles of the patient's heart at a ventricular pacing rate providing a fixed ventricular cardiac cycle in the absence of detected ventricular sense events recurring at a predetermined rate.

7. The method of claim 6 wherein the delivering step further comprises the steps of:

timing a ventricular safety delay from a ventricular pace to ensure that the ventricular vulnerable period is elapsed at the end of the ventricular safety delay; and
   delaying the delivery of the cardioversion therapy until the time-out of the ventricular safety delay.

8. The method of claim 7 wherein the step of determining a minimum blood pressure level further comprises the steps of:

providing a programmable blood pressure threshold value; and comparing the measured blood pressure value to the programmable threshold value and providing the minimum blood pressure level when the measured blood pressure value falls below the threshold value.

9. The method of claim 6 wherein the step of determining a minimum blood pressure level further comprises the steps of:

providing a programmable blood pressure threshold value; and comparing the measured blood pressure value to the programmable threshold value and providing the minimum blood pressure level when the measured blood pressure value falls below the threshold value.

10. The method of claim 6 further comprising the steps of:

incrementing the count of a cardiac cycle counter in response to a comparison that does not provide a minimum blood pressure value during a cardiac cycle; and altering the ventricular pacing rate for the succeeding ventricular cardiac cycle.

11. The method of claim 10 wherein the altering step further comprises incrementing the ventricular pacing rate.

12. The method of claim 11 wherein the altering step further comprises the steps of:

providing a programmable maximum ventricular pacing rate; and comparing the incremented ventricular pacing rate to the programmable maximum ventricular pacing rate; and providing a back-up cardioversion therapy to the patient's atria in response to a predetermined comparison of incremented ventricular pacing rate to the programmable maximum ventricular pacing rate.

13. The method of claim 12 further comprising the steps of:

providing a back-up cardioversion therapy to the patient's atria in response to a comparison that does not provide a minimum blood pressure value during a cardiac cycle.

14. The method of claim 5 further comprising the steps of:

providing a back-up cardioversion therapy to the patient's atria in response to a comparison that does not provide a minimum blood pressure value during a cardiac cycle.

15. A method of effecting cardioversion of a chamber of a patient's heart between at least one cardioversion electrode pair arranged with respect to the chamber at a minimal cardioversion energy comprising the steps of:

detecting a tachyarrhythmia of the heart chamber;

monitoring the respiratory cycle of the patient;

determining an optimum point or phase of the respiratory cycle affecting the volume of the patient's lungs and the impedance between the cardioversion electrode pair;

measuring intracardiac blood pressure of the heart during a cardiac cycle for deriving a measured blood pressure value;

determining a minimum blood pressure level; and delivering a cardioversion therapy across the electrode pairs timed to substantially coincide with the minimum blood pressure level coincidentally with the determined optimum point or phase of the respiratory cycle.

16. The method of claim 15 wherein the delivering step further comprising the steps of:

determining a ventricular pace or sense event of the ventricular cardiac cycle;

timing a ventricular safety delay from the ventricular pace or sense event to ensure that the ventricular vulnerable period is elapsed at the end of the ventricular safety delay; and delaying the delivery of the cardioversion therapy until the time-out of the ventricular safety delay, if necessary.

17. The method of claim 15 wherein the step of determining a point or phase of the respiratory cycle further comprises determining the point or phase of end inspiration of the respiratory cycle effecting the compression of the volume of the heart chamber.

18. The method of claim 15 further comprising the steps of:

timing out a therapy time; and providing a back-up cardioversion therapy to the patient's heart chamber in response to a failure to determine said optimum point or phase of the respiratory cycle during the therapy time.

19. The method of claim 15 wherein the step of determining a minimum blood pressure level further comprises the steps of:

providing a programmable blood pressure threshold value; and comparing the measured blood pressure value to the programmable threshold value and providing the minimum blood pressure level when the measured blood pressure value falls below the threshold value.

20. The method of claim 19 further comprising the steps of:

incrementing the count of a cardiac cycle counter in response to a comparison that does not provide a minimum blood pressure value during a cardiac cycle; and providing a back-up cardioversion therapy to the patient's heart chamber in response to a predetermined count of the cardiac cycle counter.

21. The method of claim 15 further comprising the steps of:

timing out a therapy time;

providing a back-up cardioversion therapy to the patient's heart chamber in response to a comparison that does not provide a minimum blood pressure value during a cardiac cycle within the therapy time.

22. A method of effecting cardioversion of the atria of a patient's heart between at least one cardioversion electrode pair arranged with respect to the atria at a minimal cardioversion energy comprising the steps of:

detecting a tachyarrhythmia of the atria;

monitoring the respiratory cycle of the patient;

determining an optimum point or phase of the respiratory cycle affecting the volume of the patient's lungs and the impedance between the electrode pair;

measuring intracardiac blood pressure during a cardiac cycle for deriving a measured blood pressure value;

determining a minimum blood pressure level in the atria; and delivering a cardioversion therapy across the electrode pairs timed to substantially coincide with the minimum blood pressure level coincidentally with the determined optimum point or phase of the respiratory cycle.

23. The method of claim 22 wherein the delivering step further comprising the steps of:

determining a ventricular pace or sense event of the ventricular cardiac cycle;

timing a ventricular safety delay from the ventricular pace or sense event to ensure that the ventricular vulnerable period is elapsed at the end of the ventricular safety delay; and delaying the delivery of the cardioversion therapy until the time-out of the ventricular safety delay, if necessary.

24. The method of claim 22 wherein the atrial cardioversion electrodes are located in substantial contact with the atria and the step of determining a point or phase of the respiratory cycle further comprises determining the point or phase of end inspiration of the respiratory cycle effecting the compression of the volume of the atria.

25. The method of claim 22 wherein the step of monitoring the respiratory cycle comprises the steps of:

incrementing the count of a respiratory cycle counter at the end of a respiratory cycle in response to a failure to determine the optimum inspiration point or phase during a preceding respiratory cycle; and providing a back-up cardioversion therapy to the patient's atria in response to a predetermined count of the respiratory cycle counter.

26. The method of claim 22 further comprising the steps of:

incrementing the count of a cardiac cycle counter in response to a comparison that does not provide a minimum blood pressure value during a cardiac cycle; and providing a back-up cardioversion therapy to the patient's atria in response to a predetermined count of the cardiac cycle counter.

27. The method of claim 22 further comprising the steps of:

timing out a therapy time;

providing a back-up cardioversion therapy to the patient's heart chamber in response to a comparison that does not provide a minimum blood pressure value during a cardiac cycle within the therapy time.

28. The method of claim 22 further comprising the steps of:

timing out a therapy time; and providing a back-up cardioversion therapy to the patient's heart chamber in response to a failure to determine said optimum point or phase of the respiratory cycle during the therapy time.

29. Apparatus for effecting cardioversion between cardioversion electrodes implanted in a patient's body comprising:

means for detecting a tachyarrhythmia of a heart chamber;

means for measuring intracardiac blood pressure during a cardiac cycle for deriving a measured blood pressure value;

means for determining a minimum blood pressure level; and means for delivering a cardioversion therapy across the cardioversion electrodes timed to substantially coincide with the minimum blood pressure level.

30. The apparatus of claim 29 wherein the means for determining a minimum blood pressure level further comprises:

means for providing a programmable blood pressure threshold value; and means for comparing the measured blood pressure value to the programmable threshold value and providing the minimum blood pressure level when the measured blood pressure value falls below the threshold value.

31. The apparatus of claim 29 wherein the delivering step further comprising:

means for detecting ventricular depolarizations and providing ventricular sense event signals in response thereto;

means for timing a ventricular safety delay from the ventricular sense event signal to ensure that the ventricular vulnerable period is elapsed at the end of the ventricular safety delay; and means for delaying the delivery of the cardioversion therapy until the time-out of the ventricular safety delay, if necessary.

32. The apparatus of claim 29 further comprising:

means for detecting ventricular depolarizations and providing ventricular sense event signals in response thereto;

means for determining a ventricular cardiac cycle from successive ventricular sense event signals;

means for incrementing the count of a cardiac cycle counter at the end of a ventricular cardiac cycle in response to a comparison during the cardiac cycle that does not provide a minimum blood pressure value during a cardiac cycle; and means for providing a back-up cardioversion therapy to the patient's heart chamber in response to a predetermined count of the cardiac cycle counter.

33. Apparatus for effecting atrial cardioversion between atrial cardioversion electrodes implanted in relation to the atria of a patient's heart comprising:

means for detecting an atrial tachyarrhythmia;

means for measuring intracardiac blood pressure during a cardiac cycle for deriving a measured blood pressure value;

means for determining a minimum blood pressure level during the cardiac cycle; and means for delivering a cardioversion therapy across the atrial cardioversion electrodes timed to substantially coincide with the minimum blood pressure level.

34. The apparatus of claim 33 further comprising:

means for detecting atrial depolarizations of the heart and providing atrial sense event signals;

means for detecting ventricular depolarizations of the heart and providing ventricular sense event signals; and means for pacing the ventricles of the patient's heart at a ventricular pacing rate providing a fixed ventricular cardiac cycle in the absence of detected ventricular sense events recurring at a predetermined rate.

35. The apparatus of claim 33 further comprising:

means for timing out a therapy time in response to detection of a tachyarrhythmia; and means for providing a back-up cardioversion therapy to the patient's atria in response to a comparison that does not provide a minimum blood pressure value during the therapy time.

36. The apparatus of claim 33 further comprising:

means for providing a back-up cardioversion therapy to the patient's atria in response to a comparison that does not provide a minimum blood pressure value during a cardiac cycle.

37. The apparatus of claim 34 wherein the delivering step further comprises:

means for timing a ventricular safety delay from a ventricular pace to ensure that the ventricular vulnerable period is elapsed at the end of the ventricular safety delay; and means for delaying the delivery of the cardioversion therapy until the time-out of the ventricular safety delay.

38. The apparatus of claim 37 wherein the means for determining a minimum blood pressure level further comprises:

means for providing a programmable blood pressure threshold value; and means for comparing the measured blood pressure value to the programmable threshold value and providing the minimum blood pressure level when the measured blood pressure value falls below the threshold value.

39. The apparatus of claim 34 wherein the means for determining a minimum blood pressure level further comprises:

means for providing a programmable blood pressure threshold value; and means for comparing the measured blood pressure value to the programmable threshold value and providing the minimum blood pressure level when the measured blood pressure value falls below the threshold value.

40. The apparatus of claim 34 further comprising:

means for incrementing the count of a cardiac cycle counter in response to a comparison that does not provide a minimum blood pressure value during a cardiac cycle; and means for altering the ventricular pacing rate for the succeeding ventricular cardiac cycle.

41. The apparatus of claim 40 wherein the altering means further comprises means for incrementing the ventricular pacing rate.

42. The apparatus of claim 41 wherein the altering step further comprises:

means for providing a programmable maximum ventricular pacing rate; and means for comparing the incremented ventricular pacing rate to the programmable maximum ventricular pacing rate; and means for providing a back-up cardioversion therapy to the patient's atria in response to a predetermined comparison of incremented ventricular pacing rate to the programmable maximum ventricular pacing rate.

43. The apparatus of claim 42 further comprising:

means for providing a back-up cardioversion therapy to the patient's atria in response to a comparison that does not provide a minimum blood pressure value during a cardiac cycle.

44. Apparatus for effecting cardioversion of a chamber of a patient's heart between at least one cardioversion electrode pair arranged with respect to the chamber at a minimal cardioversion energy comprising:

means for detecting a tachyarrhythmia of the heart chamber;

means for monitoring the respiratory cycle of the patient;

means for determining an optimum point or phase of the respiratory cycle affecting the volume of the patient's lungs and the impedance between the cardioversion electrode pair;

means for measuring intracardiac blood pressure during a cardiac cycle for deriving a measured blood pressure value;

means for determining a minimum blood pressure level; and means for delivering a cardioversion therapy across the electrode pairs timed to substantially coincide with the minimum blood pressure level coincidentally with the determined optimum point or phase of the respiratory cycle.

45. The apparatus of claim 44 wherein the delivering means further comprises:

means for determining a ventricular pace or sense event of the ventricular cardiac cycle;

means for timing a ventricular safety delay from the ventricular pace or sense event to ensure that the ventricular vulnerable period is elapsed at the end of the ventricular safety delay; and means for delaying the delivery of the cardioversion therapy until the time-out of the ventricular safety delay, if necessary.

46. The apparatus of claim 44 wherein the means for determining a point or phase of the respiratory cycle further comprises means for determining the point or phase of end inspiration of the respiratory cycle effecting the compression of the volume of the heart chamber.

47. The apparatus of claim 44 further comprising:

means for timing out a therapy time; and means for providing a back-up cardioversion therapy to the patient's heart chamber in response to a failure to determine said optimum point or phase of the respiratory cycle during the therapy time.

48. The apparatus of claim 44 wherein the means of determining a minimum blood pressure level further comprises:

means for providing a programmable blood pressure threshold value; and means for comparing the measured blood pressure value to the programmable threshold value and providing the minimum blood pressure level when the measured blood pressure value falls below the threshold value.

49. The apparatus of claim 48 further comprising:

means for incrementing the count of a cardiac cycle counter in response to a comparison that does not provide a minimum blood pressure value during a cardiac cycle; and means for providing a back-up cardioversion therapy to the patient's heart chamber in response to a predetermined count of the cardiac cycle counter.

50. The apparatus of claim 44 further comprising:

means for timing out a therapy time;

means for providing a back-up cardioversion therapy to the patient's heart chamber in response to a comparison that does not provide a minimum blood pressure value during a cardiac cycle within the therapy time.

51. Apparatus for effecting cardioversion of the atria of a patient's heart between at least one cardioversion electrode pair arranged with respect to the atria at a minimal cardioversion energy comprising:

means for detecting a tachyarrhythmia of the atria;

means for monitoring the respiratory cycle of the patient;

means for determining an optimum point or phase of the respiratory cycle affecting the volume of the patient's lungs and the impedance between the electrode pair;

means for measuring intracardiac blood pressure during a cardiac cycle for deriving a measured blood pressure value;

means for determining a minimum blood pressure level; and means for delivering a cardioversion therapy across the electrode pairs timed to substantially coincide with the minimum blood pressure level coincidentally with the determined optimum point or phase of the respiratory cycle.

52. The apparatus of claim 51 wherein the delivering means further comprises:

means for determining a ventricular pace or sense event of the ventricular cardiac cycle;

means for timing a ventricular safety delay from the ventricular pace or sense event to ensure that the ventricular vulnerable period is elapsed at the end of the ventricular safety delay; and means for delaying the delivery of the cardioversion therapy until the time-out of the ventricular safety delay, if necessary.

53. The apparatus of claim 51 wherein the atrial cardioversion electrodes are located in substantial contact with the atria and the means for determining a point or phase of the respiratory cycle further comprises means for determining the point or phase of end inspiration of the respiratory cycle effecting the compression of the volume of the atria.

54. The apparatus of claim 51 wherein the means for monitoring the respiratory cycle comprises:

means for incrementing the count of a respiratory cycle counter at the end of a respiratory cycle in response to a failure to determine the optimum inspiration point or phase during a preceding respiratory cycle; and means for providing a back-up cardioversion therapy to the patient's atria in response to a predetermined count of the respiratory cycle counter.

55. The apparatus of claim 51 further comprising:

means for incrementing the count of a cardiac cycle counter in response to a comparison that does not provide a minimum blood pressure value during a cardiac cycle; and means for providing a back-up cardioversion therapy to the patient's atria in response to a predetermined count of the cardiac cycle counter.

56. The apparatus of claim 51 further comprising:

means for timing out a therapy time;

means for providing a back-up cardioversion therapy to the patient's heart chamber in response to a comparison that does not provide a minimum blood pressure value during a cardiac cycle within the therapy time.

57. The apparatus of claim 51 further comprising:

means for timing out a therapy time; and means for providing a back-up cardioversion therapy to the patient's heart chamber in response to a failure to determine said optimum point or phase of the respiratory cycle during the therapy time.

* * * * *